(12) United States Patent
Dutta et al.

(10) Patent No.: US 10,751,259 B1
(45) Date of Patent: Aug. 25, 2020

(54) SMART BOTTLE SYSTEM AND METHODS THEREOF

(71) Applicants: Achyut Kumar Dutta, Sunnyvale, CA (US); Sudeep Hiroshi Dutta, Sunnyvale, CA (US)

(72) Inventors: Achyut Kumar Dutta, Sunnyvale, CA (US); Sudeep Hiroshi Dutta, Sunnyvale, CA (US)

(73) Assignee: Banpil Photonics, Inc., Santa Clara, CA (US)

( * ) Notice: Subject to any disclaimer, the term of this patent is extended or adjusted under 35 U.S.C. 154(b) by 0 days.

(21) Appl. No.: 16/154,702

(22) Filed: Oct. 8, 2018

Related U.S. Application Data

(60) Provisional application No. 62/569,969, filed on Oct. 9, 2017.

(51) Int. Cl.
| | |
|---|---|
| *A61J 7/04* | (2006.01) |
| *G16H 20/10* | (2018.01) |
| *B65D 51/24* | (2006.01) |
| *A61J 1/03* | (2006.01) |

(52) U.S. Cl.
CPC .............. *A61J 7/0481* (2013.01); *A61J 1/03* (2013.01); *A61J 7/0418* (2015.05); *A61J 7/0436* (2015.05); *A61J 7/0472* (2013.01); *B65D 51/24* (2013.01); *G16H 20/10* (2018.01)

(58) Field of Classification Search
CPC .......... A61J 1/03; A61J 7/0481; A61J 7/0472; A61J 7/02; A61J 7/04; A61J 7/0409; A61J 7/0418; A61J 7/0427; A61J 7/0436; G16H 20/10
See application file for complete search history.

(56) References Cited

U.S. PATENT DOCUMENTS

| | | | |
|---|---|---|---|
| 8,754,769 B2 * | 6/2014 | Stein | A61J 7/0418 340/540 |
| 2001/0028308 A1 * | 10/2001 | De La Huerga | A61M 5/14212 340/573.1 |
| 2014/0188502 A1 * | 7/2014 | Defrank | G06F 19/3462 705/2 |
| 2016/0106622 A1 * | 4/2016 | Van De Wouw | A61J 1/03 206/534 |
| 2016/0354283 A1 * | 12/2016 | Cho | A61J 7/02 |
| 2017/0304541 A1 * | 10/2017 | Bauss | A61M 15/00 |
| 2018/0296441 A1 * | 10/2018 | Roham | A61J 7/0436 |

* cited by examiner

*Primary Examiner* — Emily C Terrell

(57) ABSTRACT

This invention relates to smart bottle system that informs the user through a display, the time and date that the contents are to be taken. More specifically, the smart bottle system provides an information to the user/patient, the time to take medication and inform the caregiver, physician, pharmacy personnel, or patient/users of missed doses, the profile, and/or the health condition of the patient/user. The bottle system may track the doses remaining in the bottle, and inform the caregiver or patient/user, or pharmacy personnel the time to get a refill of the medication. The system can able to compute the profile and/or health condition of the users, based on the medication intake, and/or missed, or users image, and can communicate with the persons located remotely by sending/receiving information.

10 Claims, 37 Drawing Sheets

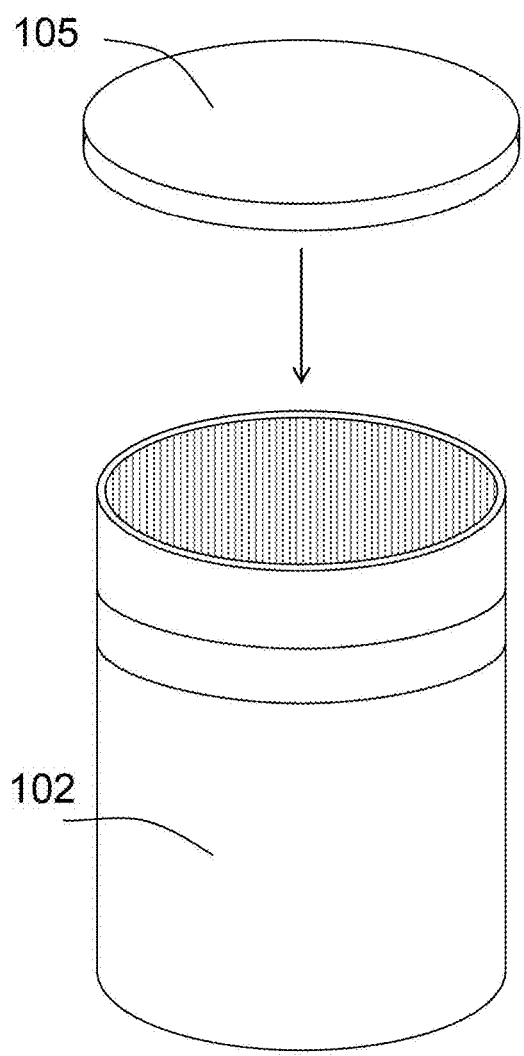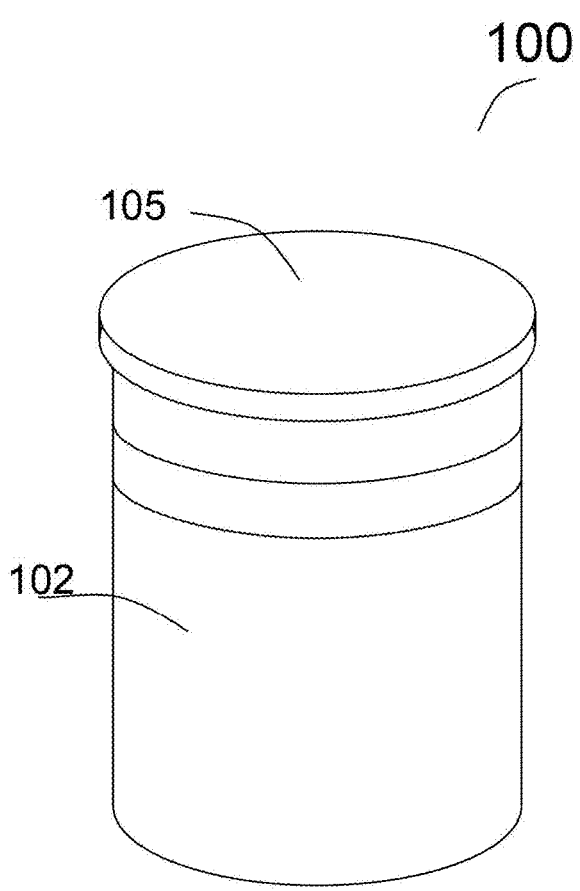
FIG. 1C
FIG. 1D

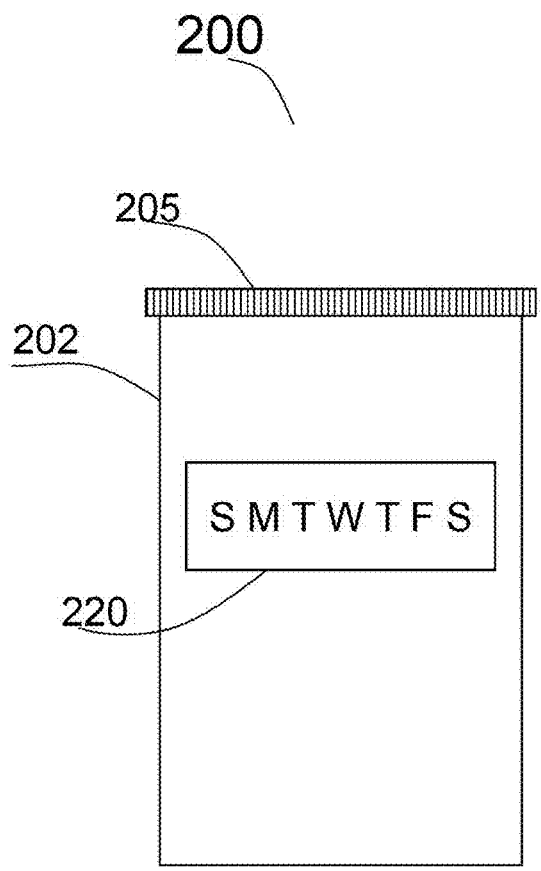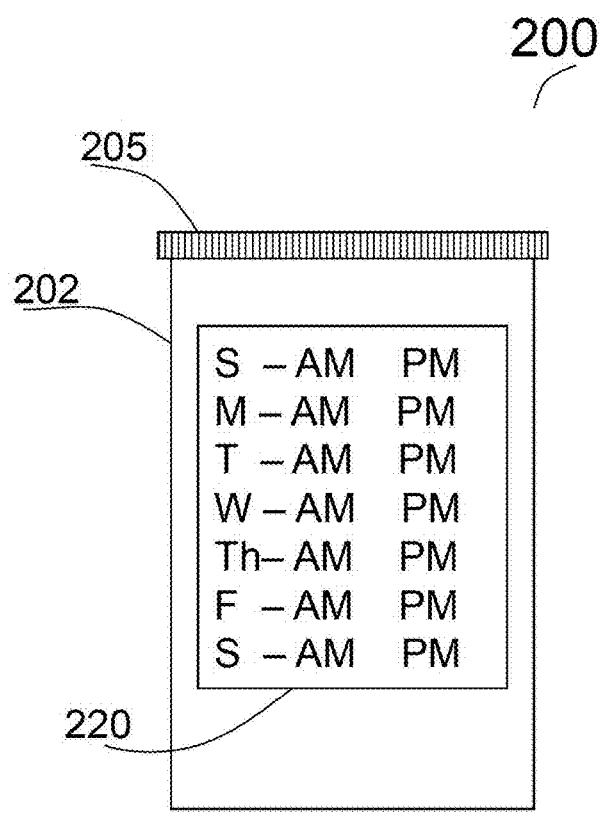
FIG. 2B
FIG. 2C

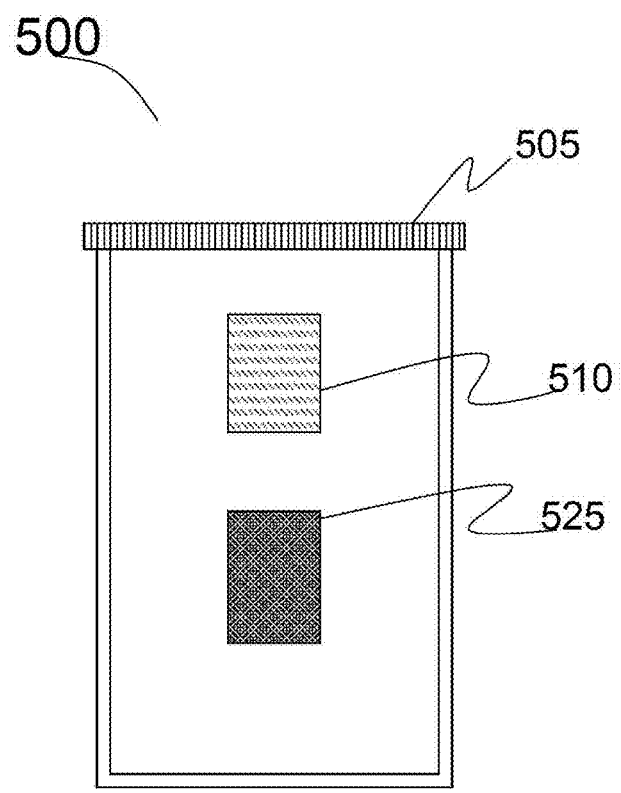
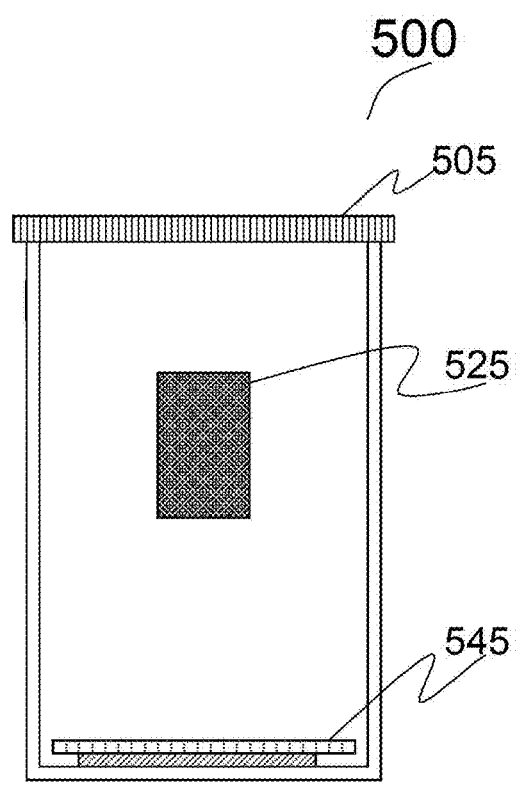
FIG. 5C
FIG. 5D

SMART BOTTLE SYSTEM AND METHODS THEREOF

CROSS-REFERENCES TO RELATED APPLICATIONS

This is an international patent application and claims priority to U.S. Provisional App No. 62/569,969 Filed Oct. 9, 2017, the provisional application is incorporated herein in its entirety.

FIELD OF INVENTION

This invention is related to bottles and containers that inform the user through a display, of the time and date that the contents are to be taken. Specifically, the bottles and containers are for the dispensing of medicine; including, but not limited to, prescribed medicines, vitamins, or supplements that need to be taken regularly, or according to a predetermined schedule. The invention allows a patient to more accurately take prescribed dosage of medication, vitamins, and/or supplements at the proper time with less/no error, thus preventing repeat doses, and missed doses of medicine as well, with less/no work needed to remember dose schedules.

BACKGROUND OF THE INVENTIONS

Modern medicine requires the frequent dosage of drugs and vitamins in the form of pills, tablets, liquid, and capsules on regimented intervals. Keeping track of the amount (i.e. doses) and time of a dose is easy for a trained professional; however, the responsibility of taking the medication often falls to the individual or patients. For many patients, such as those with disabilities or conditions that inhibit cognitive functions, taking medicine at specific times and amounts is a daunting task and this often leads to these treatments not being taken or at best, administered infrequently or at the wrong time.

There are many medicines that need to be taken at specific times or at specific intervals. These schedules can last for several weeks, months, or years, and may require several doses a day at regimented times. Solutions exist in order for patients to better track their treatment. Pill dispensers (also true from others include but not limited to liquid drug bottle or dispenser etc) help to alleviate this problem with dividers which a patient can separate their treatments into specific days and with larger containers, into time of the day. The container has a different opening for each day of the week and the patient fills their pills for each day in the containers. This process can be cumbersome, and requires the patient to fill the container weekly, remember the times when their medication is to be taken and if it needs to be administered several times a day at different time of the day. To manage their health, a patient may have several different containers filled with medications (i.e. drugs) and ready to take in each day for specific period of time. For treatments taken once/multiple times a day, such dispensers are adequate. However, when treatment varies from one to another and/or several times single or multiple medications are to be taken, then problems occur. These problems get worse for the cases of persons with ages and or brain related disease, as the cognitive ability gets affected.

Traditional bottles and dispensers have not helped patents take their medication on time. At best, the current solutions allow for a patient to organize their treatment. With these dispensers, patients often forget to take their medication or are delinquent in taking their medication. This can lead to medicine losing its effectiveness and/or patients taking multiple doses at the same time in order to make up for a missed dose. Each habit can put the patient's health in jeopardy and can lead to severe consequences.

Thus, there is a need for a pill bottle that can be programmed specifically for the dispensing needs of that medication, vitamin, or supplement, which displays the time the pill should be taken, but also tracks when the pills are taken, and indicates when the pills need to be refilled. It is more reliable for the container to remind the patient when their medication is to be taken than have the patent go to pre-filled daily containers. Such a system will result in the more reliable dispensing of medication, less missed doses and overall better patient health.

SUMMARY OF THE INVENTION

The following presents a simplified summary in order to provide a basic understanding of some novel embodiments described herein. This summary is not an extensive overview, and it is not intended to identify key/critical elements or to delineate the scope thereof. Its sole purpose is to present some concepts in a simplified form as a prelude to the more detailed description that is presented later.

It is an object to disclose a mechanism that is a multi-purpose smart bottle system (or patient med system) that functions itself to display itself its data on the MED information and/or to connect a system located to show the MED information in bottle, and/or to connect to the communications means/device (e.g., a laptop, a cell phone, a mobile device) or data device (e.g., PDA) to different peripheral devices (e.g., printers, displays, input devices, external storage entities, etc.) and networks (e.g., IP network, home networks, etc.).

The smart bottle system comprises of single or multiple sensors either located a part/whole to its bottle, or rest of the part/whole is located to close proximity to the bottle and either connected by wired or wireless (e.g. Bluetooth), electronic means which include but not limited to, sensor signal processing unit, a transmitter/receiver/transceiver, communication device. The communication device is either connected to bottle via wire or wireless (e.g. Bluetooth, home Wi-Fi). In another embodiment, the communication device may seat side by side either on a common platform and the communication device and the bottle are either physically connected via common platform or wirelessly connected. The common platform is used to supply the power to the bottle and communication device. In another embodiment, the electronic means and bottle can be located on the platform connected physically through platform or not physically connected, but located close proximity to the bottle.

According to this invention, it is an object this invention to provide a single or a multiple bottles in an alternative embodiment, which can be seated on a caddy or carrier, wherein single or multiple sensors, the electronic means, are located on it, or the sensor or electronic means can be located to the close proximity and connected to caddy/carrier by wireless connection (e.g. Bluetooth, WiFi). In another embodiment, the caddy/carrier can supply the power to the bottle, electronic means (if located on it). In further another embodiment, the communication device can seat on the caddy/carrier for power supplies and/or to get bottle information.

The smart bottle system provides a set of standard modular connectors for a wide variety of peripheral systems. The smart bottle system includes a USB hub subsystem having a set of USB ports and controller for managing connections to USB-capable devices. The smart bottle system also includes a physical network connection (e.g., Ethernet) for connecting to IP networks, for example. The USB and/or the network connection facilitate interconnecting one mobile device to another through the smart system, and/or through multiple systems.

In another preferred embodiment, the bottle a part of the smart bottle system according to this present invention is directed to a pill bottle that contains a plurality of pills, a display that provides information for the user to aid in the proper dispensation of the pills. The bottle comprises of a cap, a sensor to detect when the pill bottle when it is opened to count the time and pill left when the pills is taken. In an alternative embodiment, the bottle is connected to the power supplies means either getting directly the power from standard home supplies using the wired, or getting power wirelessly, or inductively/coactively coupled power, or energy from energy harvester device, or battery, or capacitors, or combination thereof. These can be located on the bottle and/or located to close proximity.

In the preferred embodiment, the bottle can have the biometric capability for the person/person including but not limited to the patient, caregiver, caretaker, and loved-one to open the bottle.

The preferred embodiments of the present invention are either disposable or reusable each programmed at the pharmacy to distributed the medicine, vitamins or supplements. The invention includes a pill bottle, made of plastic, glass, or another material, a photovoltaic energy harvester, a plastic cap, an electronic display, a programmable device, or small computer chip, and a sensor to detect when the bottle is opened. The display may be digital, LED, LCD, and/or another type of display. A sensor may be located in the cap of the bottle. The sensor detects when the bottle is opened and closed, each opening, and closing registering one pill or dose taken by the user.

In another embodiment, the sensor may be placed on the cap or bottle, and may be placed in several locations and have several different means of sensing the opening of the bottle. Sensors on the inside of the bottle may be photosensitive, and detect light when the bottle is opened, therefore detecting the opening of the bottle. Another sensor may be pressure sensitive and detect when the seal of the bottle is opened, therefore detecting when the bottle has been opened. Optionally an embodiment may include a pressure sensitive sensor that is combined with a child safety cap that detects when the bottle is opened. In another embodiment, the image sensor and associated lens can be also included in the bottle system, to capture the image of the patient/user, and/or surrounding to know the behavior/condition of the patient.

Another possible sensor on the bottle includes a sensor on the bottle itself that detects when the cap of the bottle is on, and when it is removed, thus allowing the sensor to detect when the cap of the bottle is removed and therefore able to count when the bottle is open to remove pills.

In the preferred embodiment, further a display is included to display the bottle information, and the display may be located on the bottle, or on the caddy/carrier, or common platform, or completely on the device, located close proximity to the bottle. The Display may be digital, LED, LCD, OLED, E-ink or any other type of display. The display may display the day that the next pill needs to be taken, or the specific time, or whether the pill should be taken in the am or PM, or if the pill should be taken before or after a certain meal. The display may be in color or not in color, and the display may have an indicator light to indicate the time the pills should be taken. Optionally the display may have a countdown timer that counts down until the time the next medication is to be taken. Optionally the display may have a light that that shines when it is time to take the medication, allowing it to stand out. Alternatively, the display may only have a light to alert and remind the user, or patient when to take the medication, similar to a notification light on a smart phone or other small appliance.

In the preferred embodiment, according to this invention, the bottle system is connected to the internet, or communication device which may be used to display and track the medication being taken by the patent, or alert the patient to a missed dose. The invention may also track the consumption of medication and inform the pharmacy when to refill the prescription. Furthermore, the invention may inform the caregiver, doctor, or family members of the patient when the patient misses a dose, or several doses so the caregiver, doctor, or family member can administer the dose, or know that the medication is not being taken so the appropriate action may be taken. Finally, the invention may monitor the health of the patient and inform care givers when of certain biostatistics. If some of these signals fall within certain ranges the bottle may contact the caregivers to alert of a problem.

To the accomplishment of the foregoing and related ends, certain illustrative aspects are described herein in connection with the following description and the annexed drawings. These aspects are indicative, however, of but a few of the various ways in which the principles disclosed herein can be employed and is intended to include all such aspects and their equivalents. Other advantages and novel features will become apparent from the following detailed description when considered in conjunction with the drawings.

BRIEF DESCRIPTION OF THE DRAWINGS

For a better understanding of the aforementioned aspects of the invention and additional aspects and embodiments thereof, reference should be made to the Detailed Description, below, in which reference numerals refer to corresponding parts throughout the figures under Drawings. The invention will be explained in more detail in conjunction with the appended drawings wherein:

FIG. 1C is the schematic of the bottle with the lid off FIG. 1D is the schematic of the bottle with lid attached to the bottle.

FIG. 2B is the schematic of alternative of a bottle with a display with a controllable LED for each day of the week in the preferred embodiment FIG. 2C is the schematic for alternative configuration of the bottle with LED display for the medicines need to be taken either single or twice a day in a week.

FIG. 5C is a schematic of alternative embodiment of a bottle showing the side-view of the bottle where the harvester and energy storage are fix onto the side of the bottle.

FIG. 5D is alternative embodiment of a bottle where the storage is attached to the side and a pressure sensor is attached to the bottom of the bottle.

FIG. 11C also illustrates of using of other functionalities of alarm, speaker for voice message.

DETAILED DESCRIPTION OF THE EMBODIMENTS

Figure 1A:
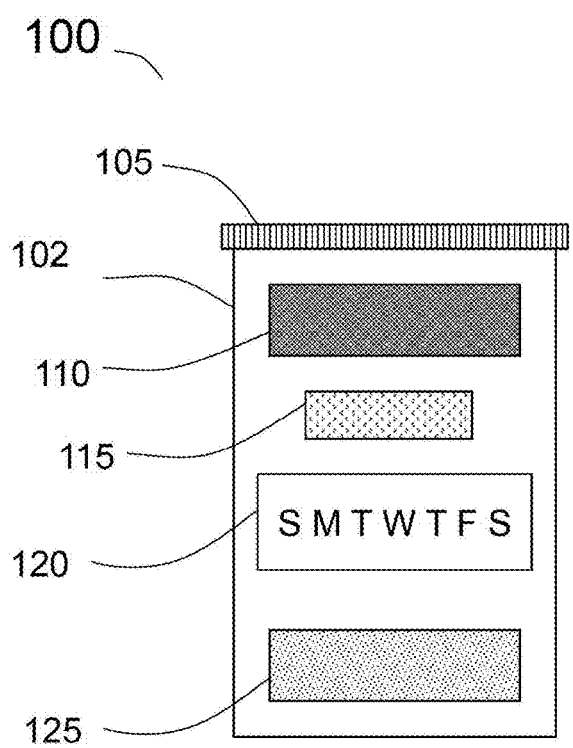
FIG. 1A is the schematics showing details of the general composition of the bottle as well as the relationship between the lid and the bottle in the preferred embodiment.

Reference is made in detail to the preferred embodiments of the invention. While the invention is described in conjunction with the preferred embodiments, the invention is not intended to be limited by these preferred embodiments. The contemplated embodiments for carrying out the present invention are described in turn with reference to the accompanying figures.

Reference numerals refer to corresponding parts labeled throughout the figures. The embodiments described herein pertain to a smart bottle system for medication taking for patient without mistake or error. The embodiments pertain to methods or techniques, and apparatuses for generating the decision in real time or close to real time for smart bottle systems.

In the following detailed description of the preferred embodiments, reference is made to the accompanying drawings, which form a part hereof, and in which is shown by way of illustration specific preferred embodiments in which the inventions may be practiced. These embodiments are described in sufficient detail to enable those skilled in the art to practice the invention and it is to be understood that other embodiments may be utilized. The following detailed description is, therefore, not to be taken in a limiting sense, and the scope of the present invention is defined only by the appended claims.

For Purposes of the Invention—Definitions

As used herein, the terms:

IoT: Internet of Things, small low power, programmable interconnected devices that can transmit and/or receive data.

Display: Any LED, LCD, E-Ink, OLED or other visual output device.

Treatment: Any medication, vitamins, elixir, syrup or any other prescribed or recommended substance by a physician or other caretaker, and/or the patient themselves. It is also mentioned as MED.

Prescription manager: An application, algorithm or another system with logic, that can aid a patient, caretaker, caregiver, or physician in tracking and taking dosages. Additionally, such a system will be able to be programmed for the recommended schedule by the physician, pharmacist or any other person qualified or unqualified to do so.

Communication Device: This is a communication means or device (mobile or fixed) including, but not limited to electronic device or means, personnel computer, mobile device, smart phone, phone, laptop, or tablet which communicate one way or multi modal way communicate to single or multiple communication devices, or bottle system. The communications device interfaces to the smart system and associated functionality via a wireless link (e.g., Bluetooth™, Wi-Fi, Wi-Max, IrDA, etc.). The communications device can be a part of the bottle system and/or can be connected physically or wirelessly to the bottle system, but when interfaces to the bottle system using a tether (e.g., mini-USB cable) via which the bottle/communication device user has more freedom to move the device/bottle.

Caddy/carrier: it is the carrier to carry or hold the bottle and/or communication device, according to this invention, and have a capability of communication with communication device. It can incorporate with the components, and/or sensors to read the real time about the bottle and/or also patient statistic data over a period of time/hr/day/month/year. The Caddy/carrier is designed into the housing such that when seated in the caddy/carrier, the bottle and/or mobile communications device is positioned and oriented for convenient user interaction with an optimum number of features such as the keypad, device display, audio output (e.g., speakers), audio input (e.g., microphone), bottle/device camera (e.g., lens for capturing images), and so on.

Private network: it is a network belongs to the individual or organization and can't be accessed by undesignated person or organization. This includes, but not limited to home network, hospital network, pharmacy network etc.

Public Network: it is a network belongs to the individual or organization and can be accessed by anyone or any organization without permission/password through WiFi connection.

Transmitter: it is an unit, a part of bottle system which can transmit the data to the desired device or communication device.

Receiver: it is a unit, a part of bottle system which can receive the data from the designated device or communication device.

Transceiver; it is a unit, a part of bottle system or separate system which can transmit and receive the data to and from the designated device or communication device, respectively.

MED: represents medication whether in solid form or liquid form, which is contained in the bottle. This MED includes, but not limited to a prescribed medication/drug to cure the disease, vitamins, and supplements.

The terminology used in the descriptions of the embodiments herein is for the purpose of describing particular embodiments only and is not intended to limit the claims. The singular articles "a," "an" and "the" are intended to include the plural forms as well, unless the context clearly indicates otherwise. It will also be understood that the term "and/or" refers to and encompasses any and all possible combinations of one or more of the associated listed terms. Similarly, the conjunction "or" is not necessarily mutually exclusive.

References will now be made in detail to embodiments, accompanied by numerals that correspond to appropriate parts of the figures. Examples will be provided to illustrate the various ways the present invention may be utilized. Specific details will be set forth to provide a thorough understanding of the present invention. However, it will be apparent to those with ordinary skill in the art that the present embodiments may be practiced without these specific details. In other instances, known methods, procedures and components have not been described in detail to avoid unnecessarily obscuring aspects of the embodiments.

FIG. 1 depicts a high level structural configuration for the pill bottle system according to this invention in the preferred embodiment. The present invention is directed to a pill bottle 100 that contains a plurality of pills (not shown here), and a display (located outside surface 102) that provides information and to aid in the proper dispensation of the pills. The bottle 100 comprises a cap/lid 105, a sensor to detect when the pill bottle 100 has been opened to count when the pills have been taken. The device is powered by an energy harvester 110 on the outside surface of the bottle 102. The preferred embodiments of the bottle itself can be made from a material so that the bottle 100 can be either a disposable or reusable bottle. The bottle 100 is either programmed at a pharmacy that distributes the medicine, vitamins or supplements, the doctors' office that prescribed the medication, and/or by the patient themselves. The bottle itself may be made out of any form of plastic, glass, or other material suitable for storing a medication/treatment within the bottle.

The pill bottle system comprises multiple subassemblies with multiple embodiments. In FIG. 1A, a pill bottle 100 comprises w a cap 105 attached to the top, an energy harvester 110, a sensor (not shown here) a programmable device 115, a display 120, attached to the bottle 102. Single sensor or multiple sensors (not shown here) can be used for counting the medication, usages, remaining etc. Additional subassemblies may be added depending on the nature of the embodiment.

The bottle 100 can be made from a variety of materials, including but not limited to plastic, glass, or metal. The bottle 100 itself may be molded, printed or cut into specific sizes depending on the size, nature, and form of the treatment. Each bottle 100 may be either disposable or reusable and can generally be designed for the specific treatment, temperament of patient and cost concerns. The bottle 100 may have recesses or other attachment points for the other subassemblies, such as screw recesses, screw cap threads, and extrusions and clips, to interlock with following subassemblies. The cap or lid 105, is attached to the top of the bottle 100 by means of screw cap but may also be done by other means (not shown here). Like the bottle, the cap 105 may be made out of a variety of materials and have similar mounts for other subassemblies.

The energy harvester 110, is attached to the outside surface 102 of the bottle 100 and is electrically connected to subassemblies in such a way that the energy harvester provides energy to the programmable device 115, to the display 120, and the sensor (not shown here). The energy harvester 110 may also gather energy from ambient electromagnetic radiation. Other types of harvesters may be used, which generates energy using source such as a motion, thermal energy, wireless power, or combination thereof Additionally, the bottle 100 can be powered by plugging in or affixed to a source of power received from other means. Finally, the bottle 100 may use any combination of the previous listed harvesters and fixed energy sources together in order to power the device.

Wireless power may be the preferred embodiment. In this version, the bottle 100 is affixed with a small inductor coupled to a non-proximate couple, radiating power (not shown here). This couple may be specifically designed for the bottle or may be a part of a general wireless power transfer station, or device located elsewhere. Other wireless power technologies may be used, such as capacitive coupling, magneto-dynamic coupling, or resonant inductive coupling, or combinations of each.

A motion energy harvester may be used to power the device. Motion harvesting may be done through the use of piezoelectric, magnet moving along a coil, or some other means. This harvester will power the device when a user handles the device, for example when picking up the device to take a pill.

Thermal energy harvesting may be another preferred embodiment. The harvester will be mounted on the bottle and use the difference between the temperature of the bottle and that of the surrounding area, or other objects such as a hand grasping the bottle. The harvester will surround the bottle in order to maximize gradient and therefore harvesting.

The energy harvester may optionally, have an energy storage device 125. The energy storage device 125 may be batteries, capacitors, or combination thereof, and would be electrically connected to the energy harvester 110, the programmable device 115, and the display 120. The energy storage device 125 provides energy to the system when no or little energy can be harvested by the energy harvester 110 which may be day harvester, or any other harvester device, mentioned earlier.

The programmable device 115, may have its function chosen by the pharmacy by pharmacy staff, at the doctor's office by the doctor or their staff, or at the residence of the patient, by the user, or a caretaker/caregiver of the user. The programmable device 115 is to be programmed with the specific dispensing schedule that the medication, vitamin, or supplement within the bottle should be dispended. The programmable device 115 may be programmed by an input device in the bottle (not shown here), or the programmable device 115 may have a transmitter or receiver and may be programmed wirelessly.

The programmable device 115 is electrically connected to the display 120 such that the programmable device 115 send the information to the display, such as the time to take the medicine and also sends the information that indicates when the display is to show an alert. A sensor (not shown here), is placed in, on or near the cap, wherein the sensor is electrically connected to the programmable device 115 and the energy harvester 110 in order to receive energy as needed from the energy harvester 110 and to signal the programmable device 115 when the sensor detects that the bottle 100 has been opened. The sensor will detect when the bottle is opened and closed. Each access to the contents will register as one pill, or dose taken by the user. Optionally the programmable device 115 may be integrated into the energy harvester 110, or the display 120 in order to miniaturized the bottle 110 and its surface 102 area on the bottle, and/or make manufacturing simpler. The controller will also have access to all of the bottle's sensors in order to properly process the information.

Figure 1B:
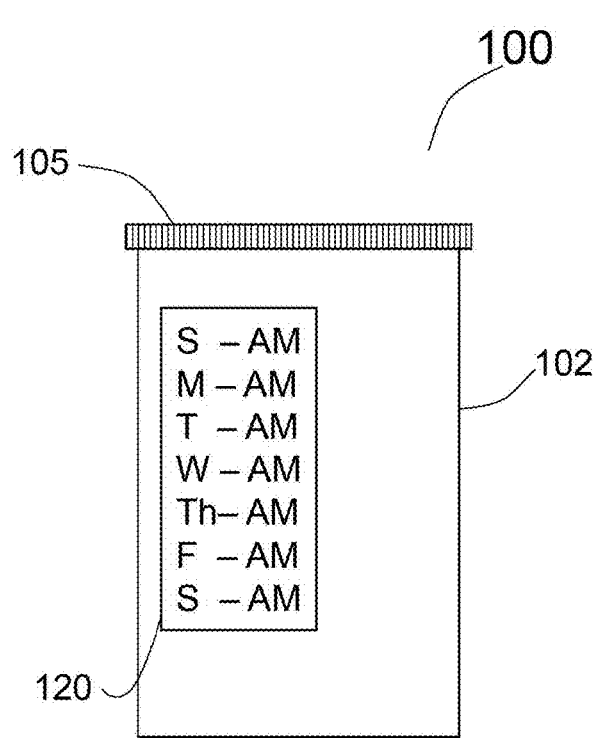
FIG. 1B is the alternative version to the bottle shown in FIG. 1A, wherein a reminder for day and time to take a dosage are included

The display 120, may be digital, LED or LCD or any other type of visual display. In this embodiment, the display has indications for day of the week, to remind the user if a treatment/medication had been taken that day. In FIG. 1B, an alternate display is shown wherein reminder for the time of day, here being AM of day, to take the medication. FIG. 1C and FIG. 1D depict how the top of the bottle may generally be attached. In this embodiment, the top is attached through pressure to the bottle. This is not the only way it may be attached and may be done through a set of threads on the cap, or other means not described here.

Figure 2A:
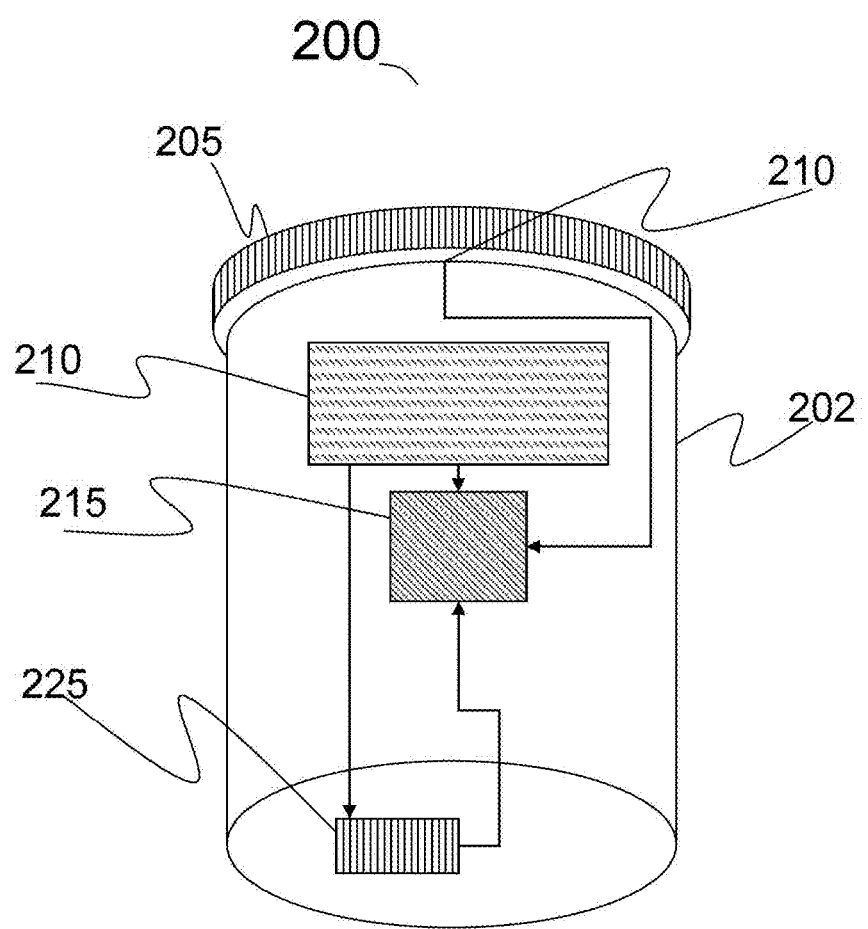
FIG. 2A is the schematic of the bottle wherein the components for electrical connections are mounted on the side of the bottle in the preferred embodiment

FIG. 2A. is the schematic of a bottle in the preferred embodiment according to this invention, showing an energy storage device 225, located on the outside of the bottom surface of the bottle, wherein the energy storage device provides energy to the integrated programmable device, and the display 220 (not shown here). FIG. 2A further depicts the electrical connections between the components. The energy harvester 210, is electrically connected to the programmable device 215, display, 220, and the energy storage device 225, in such a way that the energy harvester 210 provides energy to the programmable device/display and excess is then used to charge the battery. The programmable device is electrically connected with a sensor located in, on, near, or in proximity to the bottle cap 205, which detects when the bottle cap is opened and sends that information to the programmable device 215. Alternatively, there may be no connection between the energy harvester 210 and the battery (an embodiment of) 225, allowing the battery to be non-rechargeable, in the instance of a non-renewable battery. Optionally the display 210, and the programmable device 215, may be located separately, and they may be electrically connected such that both components receive energy sufficient to operate and communicate with each other.

FIG. 2A is the schematic of the bottles which can have several embodiments wherein the display may be represented differently on the bottle For example, varying in sizes, showing different information, and/or conveying information to the user differently. The energy harvester 210 and programmable device 215, battery (an embodiment of) 225, and other components are present, but not shown outside of FIG. 2A.

FIG. 2B shows a bottle in the preferred embodiment according to this invention, wherein the display 220, is digital, and highlights or lights up a letter indicating the day on which the dose is to be taken. This is an example of a display for medication that needs to be taken daily, and allows the patient, or a caretaker/caregiver, or medical professional know when missed days occurred. This display 220 also allows the patient to see at a glance whether they have taken medication on a given day, by means of color or light on the day, thus allowing them to remember whether they missed taking a pill, vitamin, or supplement on a given day.

FIG. 2C shows an alternative embodiment of a bottle according to this invention, wherein the display 220 is comparatively larger or having more information, and shows the days of the week and allows for separate AM and PM doses. This embodiment allowed for a simple display to inform the patient whether a scheduled dose was taken and informs when the next dose is scheduled. The display shows an AM and a PM for each day of the week. This allows the display to show two scheduled doses for each day, representing schedules that may be before, or after breakfast and dinner, or before or after bed type schedules. This embodiment may be programmed to a one time per day or one time per several days or any combination of zero, one or two doses per day scheduled throughout the week.

Figure 2D:
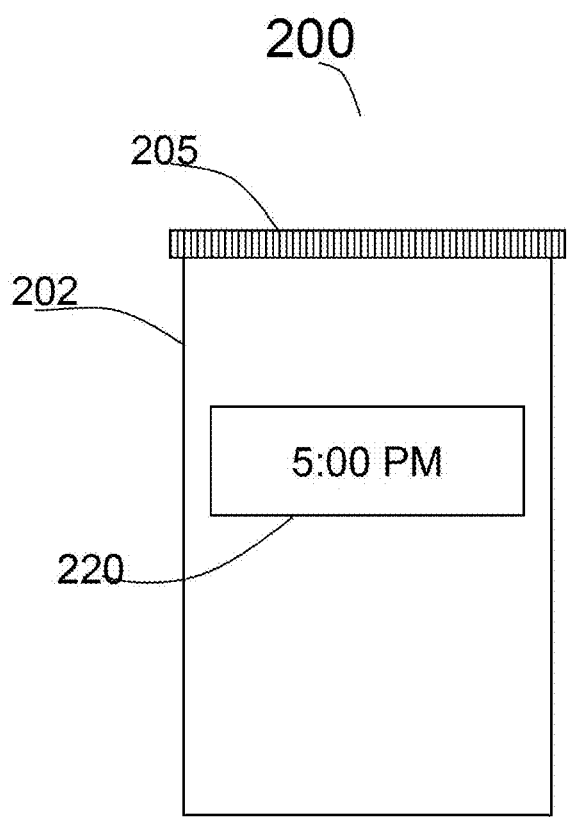
FIG. 2D shows a digital display with the time for the next dose to be administered.

FIG. 2D shows an alternate embodiment of a bottle according to this invention, wherein the display 220 is digital and displays the scheduled time the next dose is scheduled. This may operate in combination with an alarm system, not shown here. Alternatively, the display 220 may only be active after a certain time, so it shows the time the dose is to be taken a certain number of hours before. This embodiment is useful for situations wherein the doses are to be taken several times in a day to such as antibiotics that may requires 3 doses a day spread out by 8 hours.

Figure 2E:
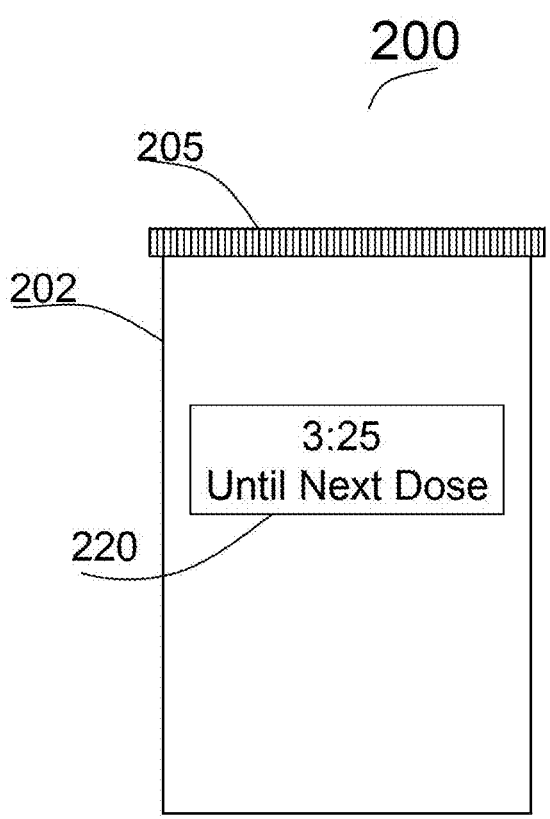
FIG. 2E shows a digital display in the preferred embodiment in which explicitly it states the time until the next dose.

FIG. 2E shows an alternative embodiment of a bottle according to this invention, wherein the display 220 is a digital display that counts down to the next dose. This allows the patient to know how long until the next dose is. This may be programmed for several times a day and is best used for medication that must be taken at certain intervolves.

Figure 2F:
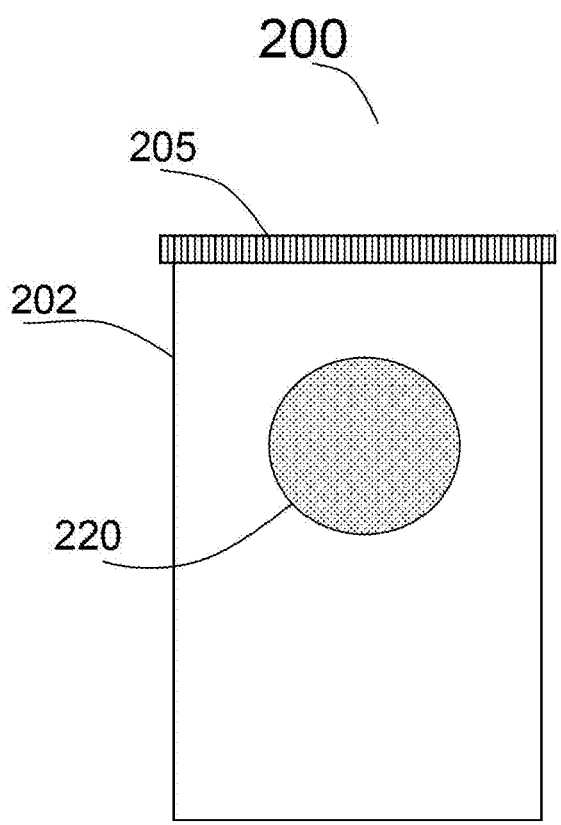
FIG. 2F shows an alter in which a LED is used, which changes color or lights up when it is time to take the medication.

FIG. 2F shows an alternate embodiment of a bottle according to this invention, wherein the display 220 is simply a light that lights up to indicate that the time to take the does has been taken. In this embodiment if the dose has been taken the light turns off, and if the dose has not been taken on that given day the tight stays on. The light does not have to be bright or on continuously, it may turn on and off periodically to preserve power, or may be dim enough not to drain power, but still noticeable to the patient upon looking at the medication.

Figure 2G:
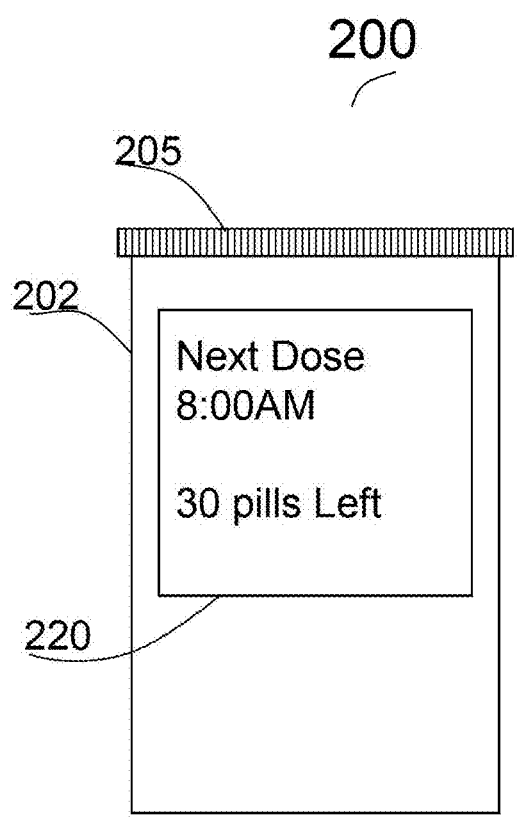
FIG. 2G shows a display which displays the time of the next dose and the number of pills left.

FIG. 2G shows an alternative embodiment of a bottle according to this invention, showing an example of a display 220, wherein the display provided the time of the next dose on a digital display and the number of remaining pills. This example is not exclusive, there are several iterations of information that this display may show, for example the display may show the remaining time until the next dose, the date of the next dose, the remaining doses to be taken that day, the number of doses to be taken before the bottle is empty, the date the bottle should be empty, how long overdue the dose is, etc. The information displayed being up to the caretaker/caregiver, physician or patient themselves.

Optionally other displays configurations may be used, including the combination of one or more of the above configurations, or other iterations of display information. For example, one of the iterations using a clock, and the light displays may be combined to show the time of the dose and to use the light as an alarm to take the medication.

FIGS. 3A to 3F show embodiments wherein the sensor is attached to the cap of the pill bottle. The sensor 330 may be attached to the outside surface of the bottle cap 305 on the inside surface of the rime of the bottle cap, on bottom surface of the rim of the bottle cap or on the bottom surface of the inside of the cap. The sensor 330 that detects when the cap is opened may be a pressure sensor, stress sensor, light sensor, accelerometer, electrical contact, camera, biometric, other type, or combination thereof. The sensor 330 may detect when the cap is opened, by either detecting light, or it may detect the stress, (pressure, compressive or share stress). Alternatively, the camera can provide also the information of the patient facial condition and others (not mentioned here) which is necessary to project the health condition of the patient using the computing device or similar means either embedded and/or outside device.

Figure 3A:
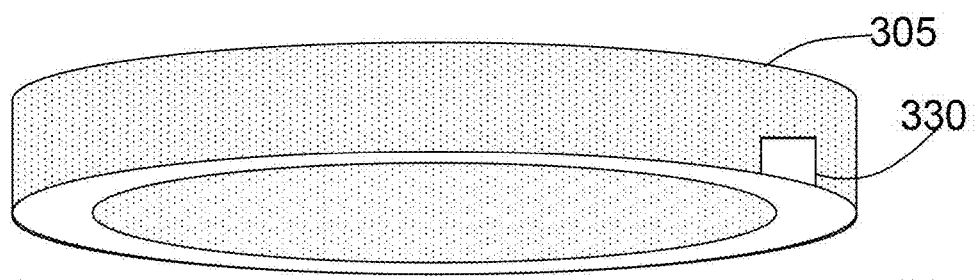
FIG. 3A shows a schematic of the lid at the cap of the bottle, in which specifically how sensors the register opening and closing as well as photovoltaic generators will be mounted.

FIG. 3A depicts an embodiment of a cap in the preferred embodiment according to this invention, wherein the sensor is attached to the outside surface of the bottle top, part 305. The sensor 330 detects the pressure placed on the pressure when the bottle top 305 is opened. This embodiment may coincide with a bottle top that is from a safety cap. Such caps are well known in the art, and are used to keep children from opening pill bottles. In the current embodiment is different from prior art and use a sensor 330 that is on the outside surface of the bottle cap, and may be placed on a button to release a locking mechanism to open the bottle. Thus, when the locking mechanism of the safety cap is unlocked the sensor detects the opening of the bottle cap. This may work either through pressure, such as having a pressure sensor detect the required pressure to open the bottle, or that the button to unlock the bottle also record the bottle being opened to count the dose being taken.

Figure 3B:
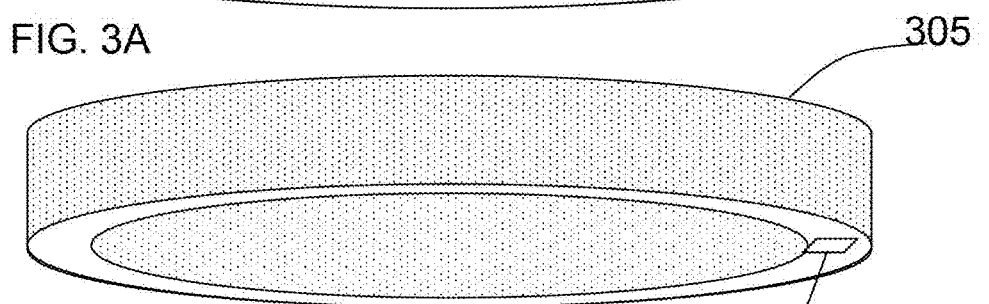
FIG. 3B is the schematic of a lid with a bottom mounted sensor.

Alternatively, a sensor 330 may be placed around the rim of the bottle cap that detects the torque applied to the bottle cap in order to open it. The sensor 330 can detect when the torque is of sufficient magnitude in the correct direction in order to count in opening the bottle. The sensor will then send the signal to the programmable device indicating that it is opened FIG. 3B depicts an alternative embodiment according to this invention, wherein the sensor 330 is placed in the bottom of the rim of the bottle cap 305, wherein the sensor then senses the removal of the cap. The sensor placed in this location may operate if various means including but not limed to stress sensor, a pressure sensor or a sensor that detects the proximity to the bottle itself. In the instance, wherein a stress or pressure sensor is used the sensor detects a change when the bottle cap is attached compared to then it is not, and sends a signal to the microprocessor. The signal indicates to the microprocessor (or microcontroller) that the bottle cap has been moved.

Figure 3C:
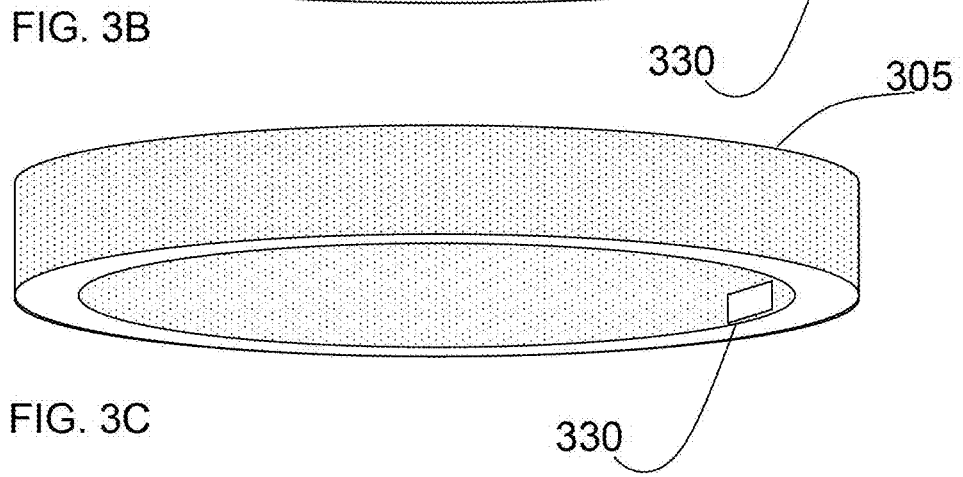
FIG. 3C is the schematic showing a lid with a side mounted sensor.

FIG. 3C depicts a bottle cap in the preferred embodiment according to this invention, wherein the sensor 330 is located on the inside rim of the bottle cap, 105. Similar to above as shown in FIG. 3A, the sensor 330 can detect the pressure to know when the bottle cap is on or off. Optionally the cap may also be an electrical contact that detects when the bottle cap is secured on the bottle or removed. Alternatively, the sheer stress changes involved in opening or closing the bottle may also be used in detecting when the bottle is opened or closed.

Figure 3D:
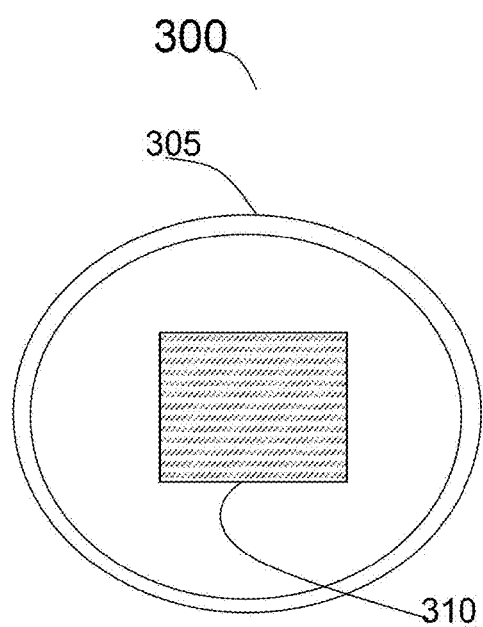
FIG. 3D is a schematic showing a lid with photovoltaic sensor that registers when the bottle is opened.
Figure 3F:
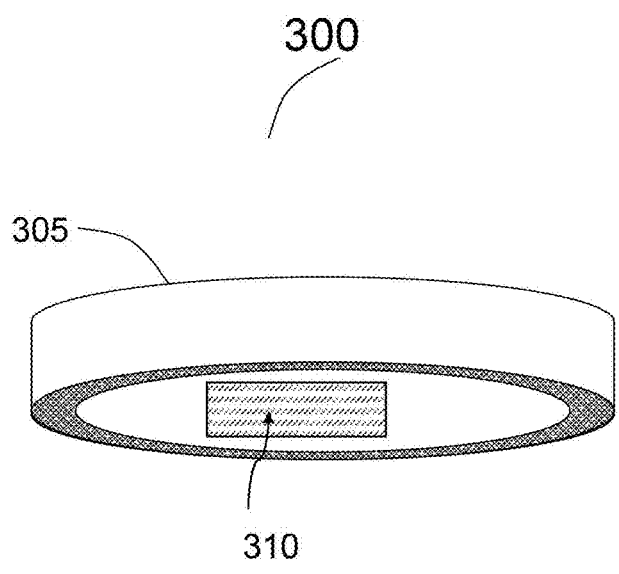
FIG. 3F is a schematic showing an alternative view of the photovoltaic sensor lid.

FIG. 3D is a schematic showing an alternative embodiment of a cap/lid, according to this invention, wherein the bottom, indices surface of the bottle cap has an energy harvester (i.e. photovoltaic cell) 310 that can act as the sensor 310 sensor that detects when the bottle is opened. FIG. 3D is a view from the bottom of the cap 305 and shows a photovoltaic sensor. The photovoltaic sensor works because pill bottle is often dark or not light permeable in order to protect the medication inside from degrading as a result from direct exposure to light. While the bottle cap 305 is on the bottle the photovoltaic sensor 310 will not detect any light or a minimum amount of light, however when the bottle is opened then the photovoltaic sensor will detect significantly more light, thus knowing when the bottle is opened.

Another embodiment involves the entire system, comprising of further electronic device (i.e. microprocessor, harvester, etc) being placed on the cap of the bottle itself. This system will require the programmable device, display, energy harvester, and sensor to be placed on the cap itself. This design has the advantage of being separate from the bottle of medication or vitamins, allowing the cap to be used on several different bottles. This embodiment will be self-powering or require a replaceable battery.

Figures 4A, 4B:
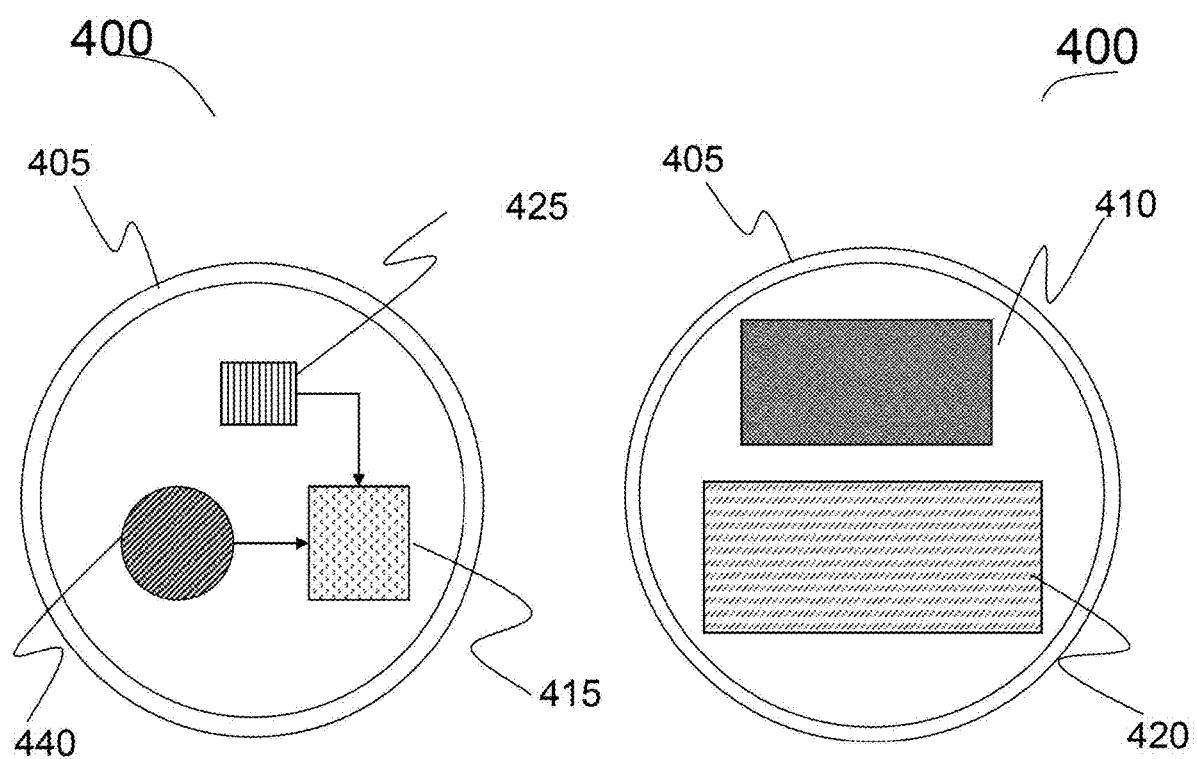
FIG. 4A is a schematic of a lid incorporating with the computational, energy storage, and sensor where they are all attached to the bottom and/or sides of the lid.
FIG. 4B is a schematic showing the top-view of the lid with a display and the energy harvester.

FIGS. 4A and 4B are the schematics showing the alternative embodiments of a cap/lid of the bottle according to this invention, wherein all of the components of the system are located in the bottle cap. FIG. 4A shows the bottom of the bottle cap 405, comprising with an energy storage device 425, a photovoltaic light sensor 440, and programmable device 415 attached to the bottom of the bottle cap, the photovoltaic light sensor 440 is similar to the one described in FIG. 3D, therefore repeated explanation is omitted here. The energy storage device and microprocessor are attached to the cap, however they are electrically connected to the components on the top of the cap as shown in FIG. 4B. The photovoltaic sensor 440 is electrically connected to the programmable device 415 and sends signal when the photovoltaic sensor 440 detects that the cap is off of the bottle. The programmable device 415 is electrically connected to the energy storage device 425, and draws energy as needed.

FIG. 4B is the schematic of a top of the cap of the bottle, the top of whose cap is shown in FIG. 4A. The embodiment shown in FIG. 4B has the solar harvester 410 and the display 420 located on the top of the bottle cap. The display on the cap may be of any type mentioned above, or depicted in FIG. 3. The components are electrically connected, through the bottle cap. The connections may be located on either the top of the cap, the bottom of the cap, inside the cap, or combination thereof.

Optionally there may be no energy storage device such that the programmable device operates off of energy from the photovoltaic energy harvester and is alerted to the opening of the bottle by the signal from the photovoltaic sensor 440.

Figure 4C:
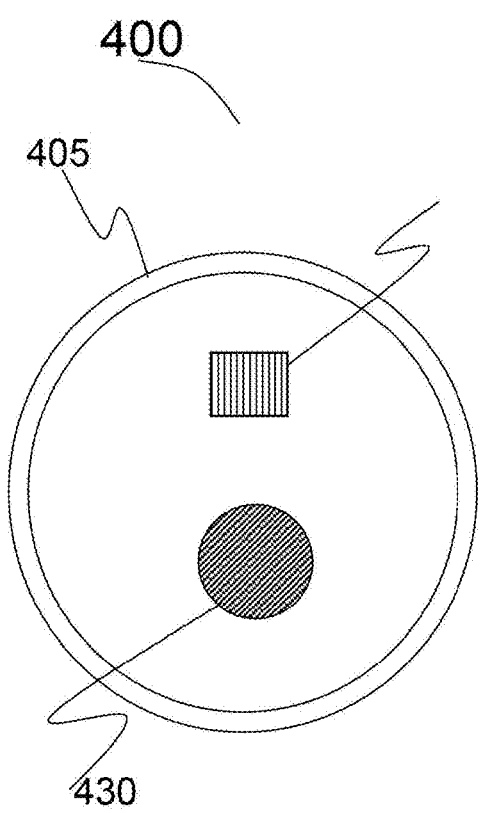
FIG. 4C is a schematic showing energy storage/generator and sender in the alternate embodiment.
Figure 4D:
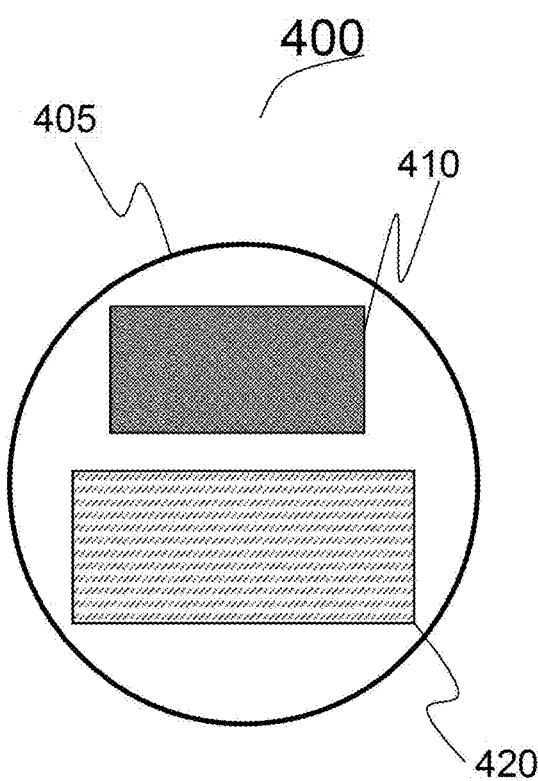
FIG. 4D is a schematic showing a top view of the lid with energy storage/generator and display of the bottle as shown in FIG. 4C.

FIGS. 4C and 4D are the schematics showing the alternative embodiments of bottle cap's bottom and top side views, according to this invention, wherein the display 420, sensor 440, battery 425, and energy harvester 410 are located on the bottle cap 405. The display 420 and programmable device (not shown here) are integrated together, and located on the top surface of the bottle cap. The energy harvester 410 is placed on the top surface of the bottle cap 405, in order to collect energy for the system. In the present embodiment, there is a photovoltaic sensor on the bottom surface of the bottle cap that can detect the increase in light when the cap is opened. Alternatively, other methods may be used as mentioned above. The battery 425 may be used in the bottle cap or optionally may be absent for the system. The battery may be used as an alternative or supplement to the energy harvester. Alternatively, battery may either be replaceable, if used without an energy harvester, or rechargeable if used with an energy harvester. Alternatively, the programmable device may be integrated directly into the energy harvester 410 instead of the display.

The bottle cap system may be reusable or it may be disposable. For example, but not to be construed as a limitation the bottle cap may be part of the bottle, programmed when the bottle is filled either at a pharmacy or another distributor, such as a store, online distributor, or doctor's office, or the bottle cap or is programmable by the patient or user, after purchase. The bottle cap is sized to be standard to common pill bottles.

Figures 5A, 5B:
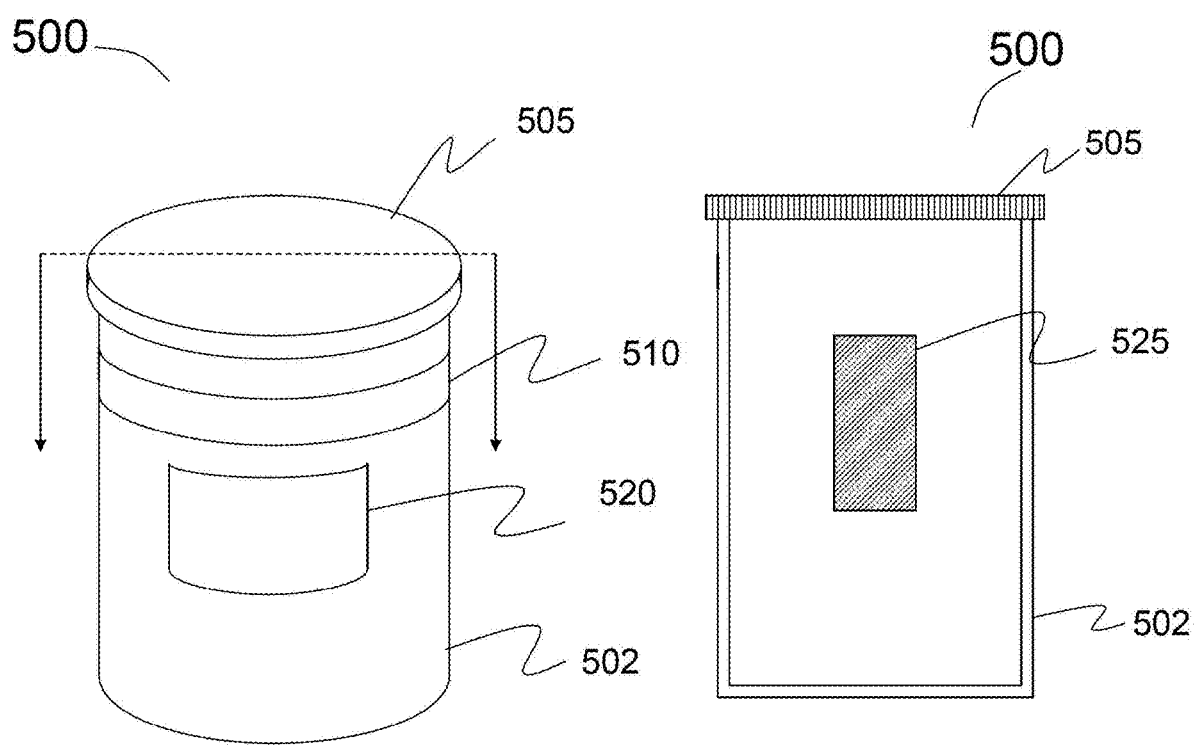
FIG. 5A is a schematic of bottle showing a energy harvesting band and display around the circumference of the bottle.
FIG. 5B is a schematic of alternative embodiment of the bottle where the energy storage is mounted on the side of the bottle.

FIGS. 5A to 5F are the schematics showing various alternative embodiment of pill bottles according to this invention, wherein similar numeral represents the similar parts as explained in FIGS. 1A to 4B, therefore repeated explanations are omitted here. FIG. 5A is an embodiment of the pill bottle design, similar to the embodiments explained earlier, however this embodiment has internal components shown to FIGS. 5B, 5C, and 5D. FIG. 5A also has an energy harvester 510 located as a strip that extends around the circumference of the bottle near the top near the cap 505 in order to provide energy to the system and display 520 located on the side of the bottle 502.

FIG. 5B is the schematic showing a cross sectional view that depicts the use of internal components, specifically the use of an internal sensor to detect when the bottle is opened. The sensor shown is a photovoltaic sensor that senses the increase in light when the bottle cap is taken off for the pills to be dispensed. When the sensor detects the light, sensor sends a signal to the programmable device, indicating that the bottle has been opened, and having that count as a dose taken.

FIG. 5C is the schematic showing a cross section of an alternative embodiment wherein pill bottle 500 has the same external components as mentioned above, however the internal components include a photovoltaic sensor as above, and an energy storage device located on the inside of bottle. Because these components are located internally in the bottle, the components may be placed in different arrangements that provide for various advantages depending on the medication, or use of the bottle. For example, the saving of outside surface area allows more room for labeling, or marketing material on the outside surface. Furthermore, because internal space is not a great demand for pill containers placing components will not adversely affect the bottles use carrying pills or medication.

FIG. 5D Depicts the schematic showing a cross section of an alternative embodiment wherein the sensor 545 is located at the bottom of the bottle and senses the weight of the tablets in the bottle. The sensor then sends that information to the microprocessor which then calculates how many more doses are remaining in the bottle, and if a dose was administered after the opening of the lid by weight difference. The information is then displayed as mentioned above. From these measurements, the programmable device will then calculate the amount left and if need be, remind the patient to order more, contact a caretaker of the low amount left and/or contact the pharmacy in order to refill the treatment.

Figure 5E:
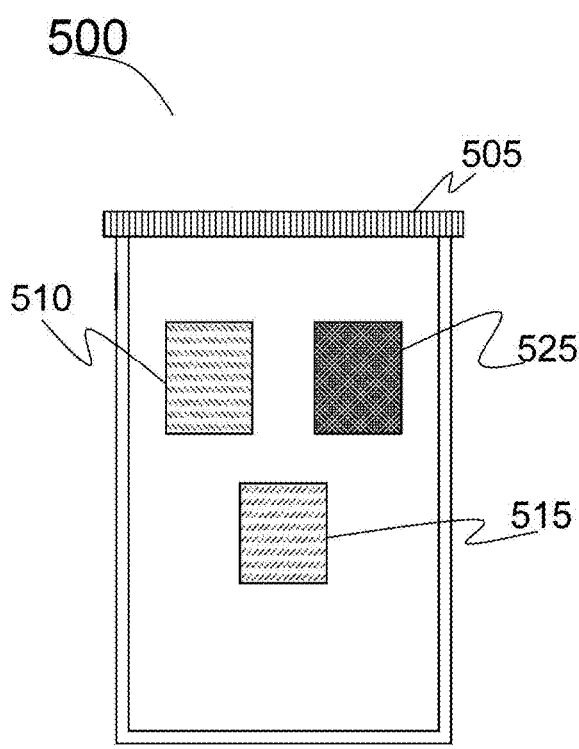
FIG. 5E is a schematic showing an alternate embodiment of a bottle, where the microcontroller, the energy harvester and energy storage are all mounted on the side of the bottle.
Figure 5F:
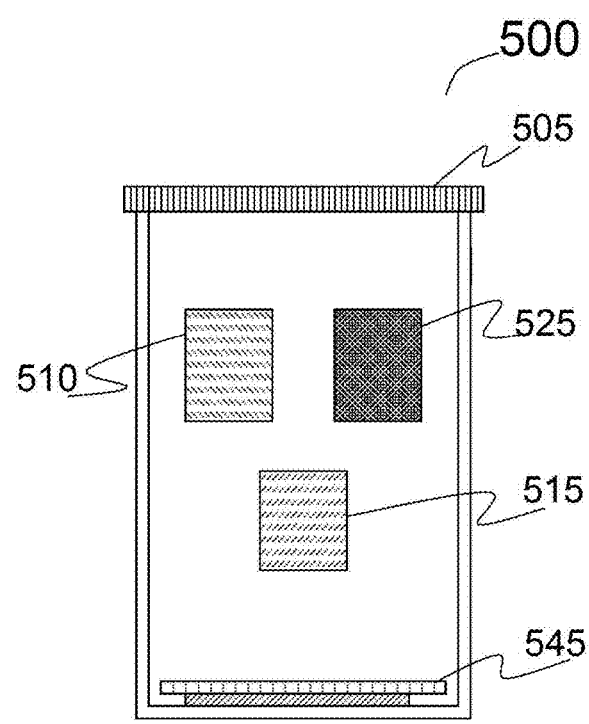
FIG. 5F is alternate embodiment of a bottle where the microcontroller, the energy harvester and energy storage are all mounted on the side of the bottle as well as a pressure sensor at the bottom of the bottle.

Alternative embodiments are further shown in FIGS. 5E and 5F wherein the programmable device is shown to be on the inside of the bottle, along with the components above.

Figure 6A:
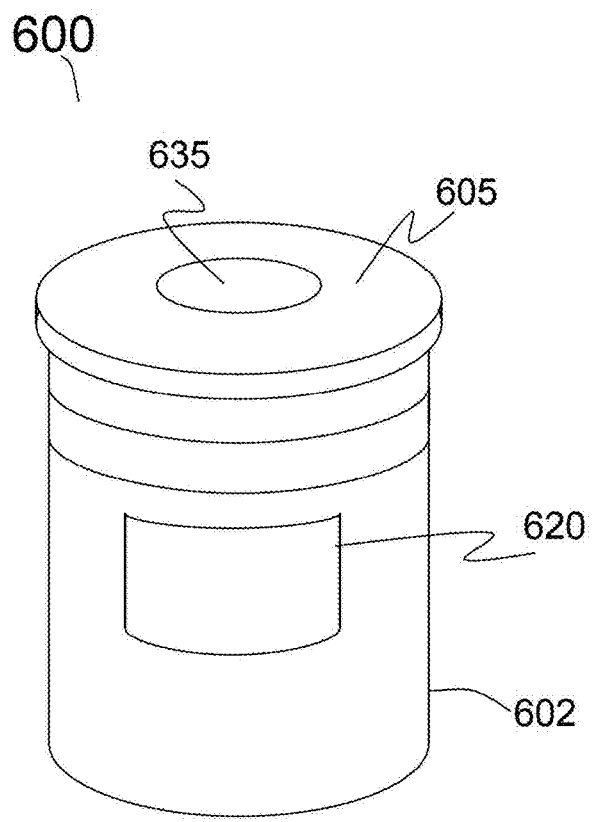
FIG. 6A shows an embodiment where the dose and/or pills remaining is done through a button counter mounted on the top of the bottle.
Figure 6B:
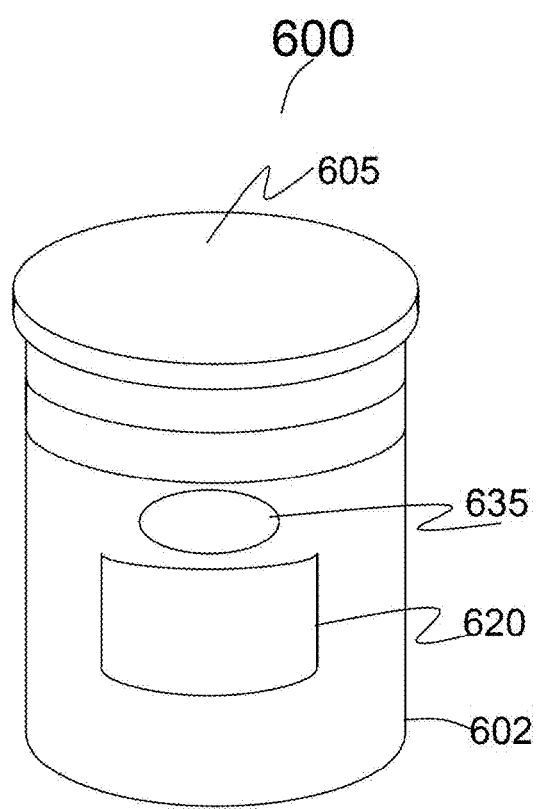
FIG. 6B shows an alternate embodiment where the dose and/or pills remaining is done through a button counter mounted at on the side of the bottle.

FIGS. 6A and 6B are the schematics showing various embodiments of the bottles according to this invention wherein similar numerals represent the similar parts; thereby the repeated explanation is omitted here. The main differences from other embodiments explained earlier are that, a button 635 is present on the bottle, in place of a sensor. In this embodiment, the bottle 600 does not detect when the bottle cap 605 is opened, such as how many pills are left, or the level of liquid remaining. In this embodiment, the patient must press the button to indicate that a dose has been taken, as an alternative to a sensor detecting that the patient has taken their scheduled dose. The button 635 may be placed at any point alongside of the bottle.

Alternatively, a button 635 may be placed or integrated into the cap or at the base of the bottle, such that the button 635 will be presses to indicate that a dose has been taken by pressing down on the bottle. This may also provide and act for child safety cap, as to open the bottle 600, the cap must have sufficient downward force applied in order to allow the cap to unscrew from the bottle. Optionally the sensor may be placed at the bottom of the bottle allowing the patient to press down on the bottle causing the bottle to register the dose has been taken.

In another embodiment, the bottle has a liquid medication. The liquid medication may be in the form of a cream, syrup, jell, elixir, or other liquid medication. This embodiment will detect when the cap is open through methods discusses above. The programmable device will then calculate the dose by taking the preprogrammed measurements programmed when the device was programmed. Furthermore, the Liquid bottle according to this invention will be very similar to the pill bottle format in that there is a display, a sensor and either or both a photovoltaic energy harvester and a battery to power the device as well as any appropriate connection to outside networks.

Figure 7:
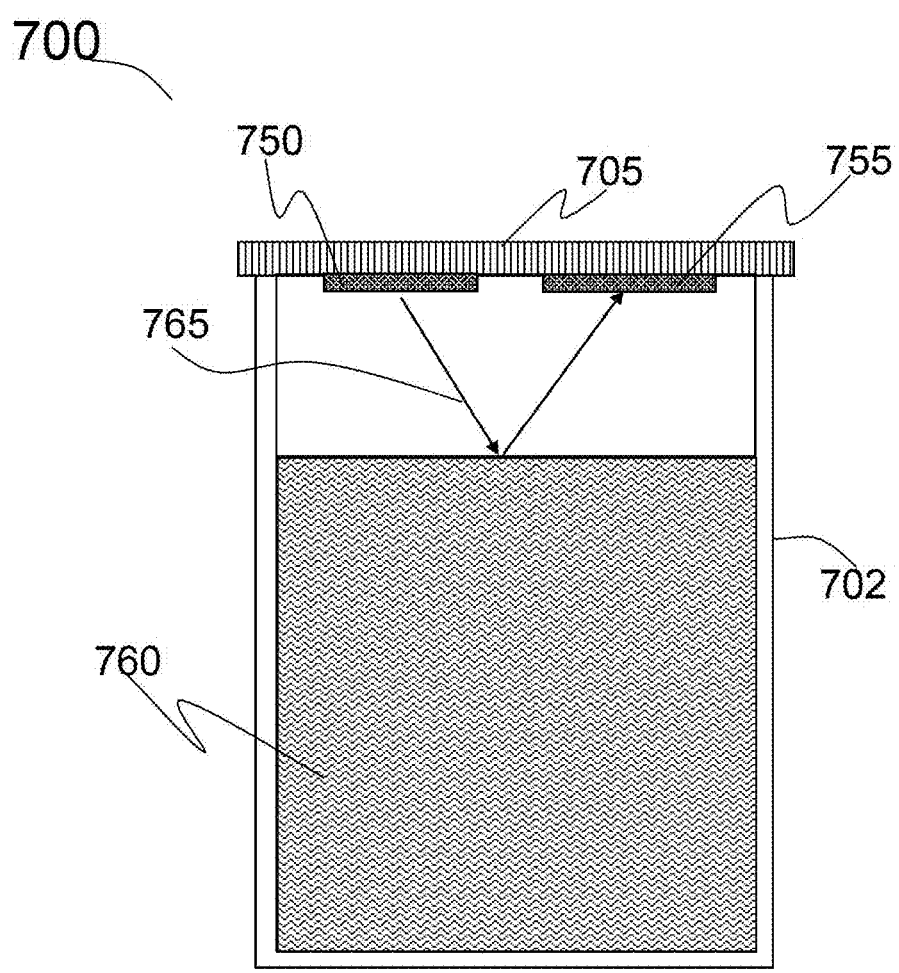
FIG. 7 is a schematic showing an embodiment of the bottle designed for liquid, with the ability to estimate the amount left.

FIG. 7 is a schematic showing the bottle in the preferred embodiment according to this invention, wherein like numeral represents the like part; therefore repeated explanation is omitted here. In FIG. 7, the bottle 700 is filled with a liquid medication, vitamin, or supplement 760. The bottle 700 depicts a light/laser transmitter 750, a receiver/detector 755, wherein the light/laser transmitter sends a light signal 765 onto the surface of the liquid medication 760 wherein the light/laser 765 reflects from the surface of the liquid and on to the receiver 755. The amount of liquid remaining is calculated by using the level of the liquid in the bottle and the area of the bottle. The programmable device, (not show here) then calculates the remaining doses, and whether or not a dose of the previous medication was taken. The light can be generated from any source such as light-emitting diode (LED) or laser diode (LD). The detector which detects the reflecting light can be single element or multiple elements, which comprises the receiver. The receiver comprises of the electronic devices and LED/LD (not shown here). The wavelengths of light to be selected for measuring the liquid level may varies and specially depend on the density/viscosity/transparency of the liquid medication.

Optionally, the bottle may utilize the methods mentioned above to determine the dose, or it may utilize a triangulation method to determine the number of doses remaining in the bottle. At the specified time, the bottle will use the light from LED/LD and a reflecting light to detector to determine the level of the liquid in the bottle. The LED/LD and receiver use a triangulation system that works by detecting the spread of the laser after reflecting off of the surface of the liquid. This works by triangulating size of the area the laser reflecting on the surface of the liquid, the larger the lasers area the lower the surface of the liquid. Optionally the bottle may display when the bottle will be employ, and need to be replaced, or refilled. In alternate embodiment, other technique such as time of arrival technique can be used to determine the length of light-path changes due to taking of the medication. The path will get longer as more times are medication is taken. The level of medication in the bottle then be calculated comparing with the initial reading and provide the data in the display.

Figure 8A:
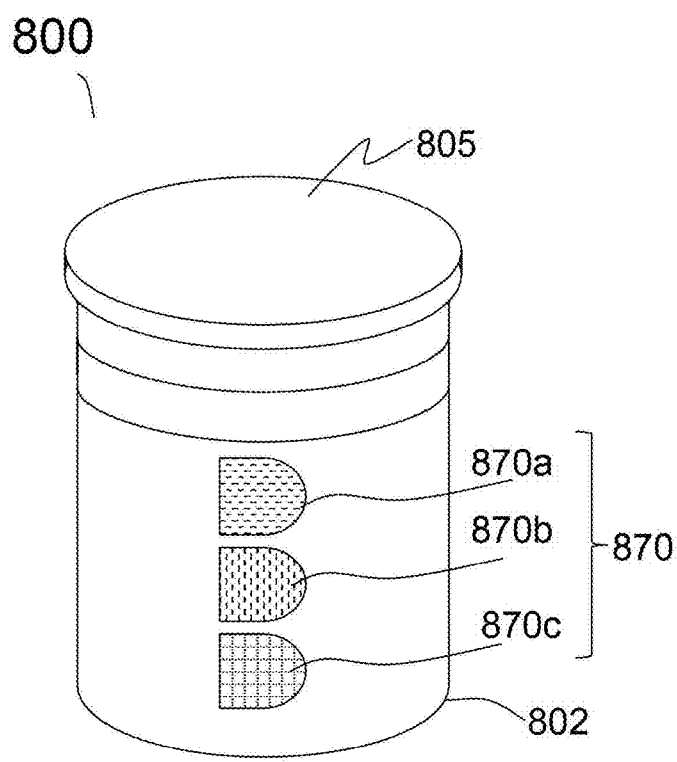
FIG. 8A is a schematic showing a bottle with a variety of biometric sensor, where the patient will grasp the bottle, here each with their own pad in the preferred embodiment.
Figure 8B:
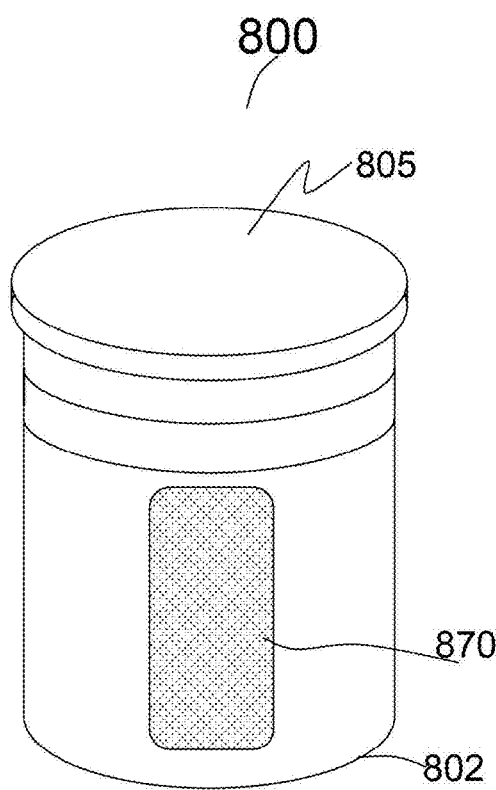
FIG. 8B is a schematic showing an alternate embodiment of a bottle with a variety of biometric sensors where the patient will grasp the bottle, here with a strip on the side of the bottle.

FIGS. 8A and 8B are the schematics showing the bottles in the preferred embodiments according to this invention wherein like numeral represents the like part, therefore the repeated explanation mentioned in FIGS. 1A to 7, are omitted here. FIG. 8A to 8B show details an embodiment where the bottle 800 has a variety of biometric sensors 870 (i.e. 870a, 870b, 870c etc) attached to the bottles. The sensors 870 include but are not limited to, an electrocardiograph monitor, a pulse oximeter, temperature, finger print sensor, facial recognition, blood pressure sensor, a proximity sensor or combination thereof. The sensors 870 can be mounted on the outside in order register inputs when the patient grasps the bottle. This information can then be relayed through wireless antennas to a caretaker/caregiver, patient's loved one, pharmacist or doctor. These measurements may be collected and can be sent individually to the caretaker, caregiver, loved-one, or in packets displaying changes over time, medication taking data, health condition, behavior etc. These large amount of information is essential and helps to know how patient is taking medication and how health is responding to medication intake, and allowing the person/physician or others to diagnosis the health condition during office visit and/or off-site (without looking at the patient, to know the health condition of patient Additionally, if any one metric is in a dangerous range, then the bottle may give a visible, physical, or audible cue in order to warn the patient, or may contact their physicians, emergency personnel, loved family members, and/or combination thereof. The sensors 870 may be mounted along the bottle in order to make contact with a patent's fingers when they grasp the bottle. This can be done with a channel, as shown in FIG. 8A or as a long strip as shown in FIG. 8B.

Figure 9A:
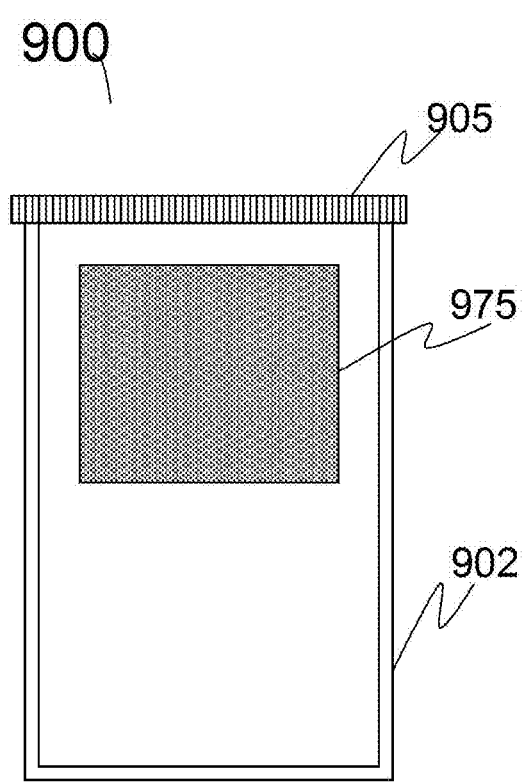
FIG. 9A is a schematic of a bottle incorporating with a camera to register the action/condition of a patient taking the medication and/or also, with the sensor on the side.
Figure 9B:
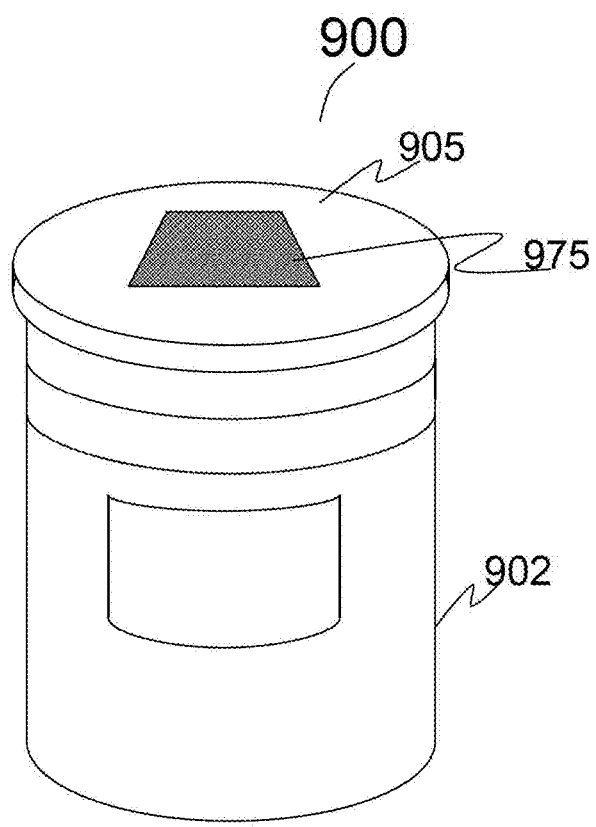
FIG. 9B is a schematic showing an alternate embodiment of a bottle incorporating with a image sensing device and/or with the sensor on the cap of the bottle.
Figure 9C:
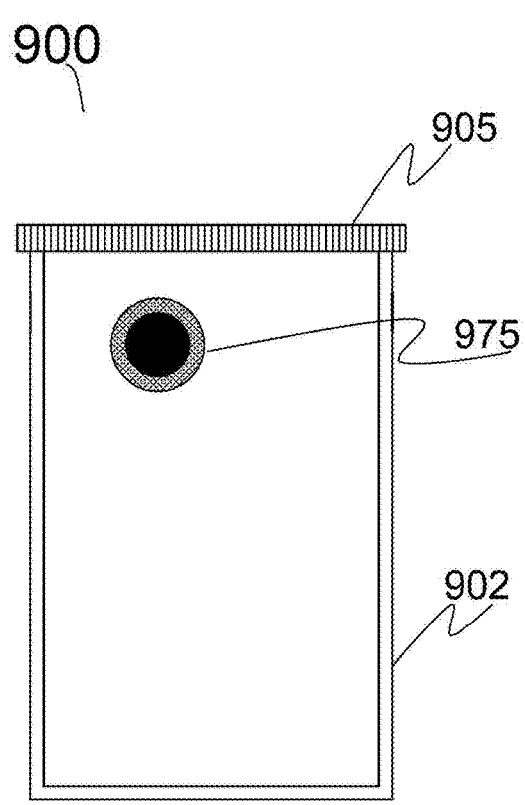
FIG. 9C is a schematic showing an alternate embodiment of a bottle with image sensing with a lens covered sensor on the side of the bottle.
Figure 9D:
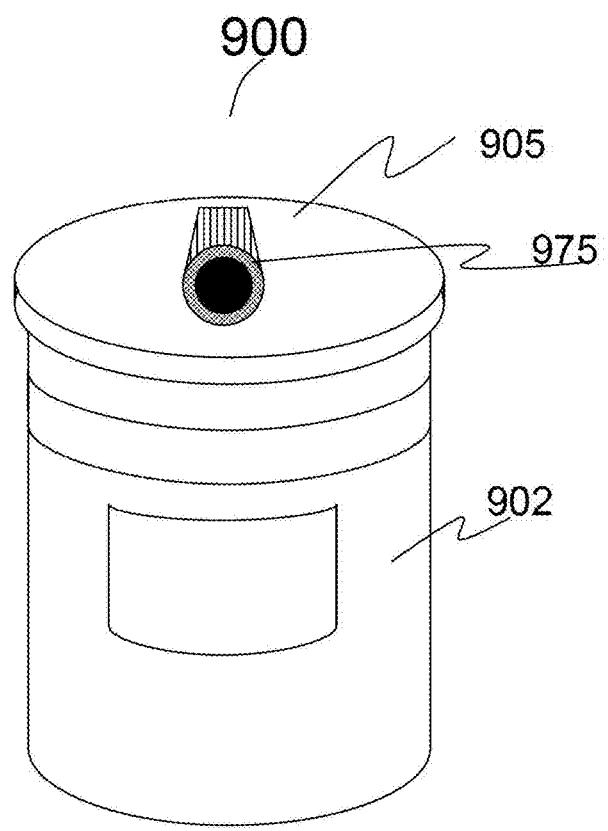
FIG. 9D is a schematic showing an alternate embodiment of a bottle having capability of image sensing with a lens covered on the top of the bottle.

FIGS. 9A to 9D are the schematics showing the bottles in the preferred embodiments according to this invention wherein like numeral represents the like part, therefore the repeated explanation mentioned in FIGS. 1A to 8, are omitted here. In FIGS. 9A to 9D, the bottle is affixed with an image sensor 975, that can take the image and can be used to detect the patient health condition through facial image, when the patient has taken their medicine. This information is relayed to microprocessor, 915 (not shown here) and computation can either be done on the processor or sent packets to other devices and or communication device to register the taking of medicine. The sensor 975 in FIGS. 9A to 9D is attached to the bottle 902 or the cap 905 of the bottle. This allows for ideal capture of information when the bottle is inside a medicine cabinet. Based on the type of medicine cabinet types (especially wherein the door is with cabinet) image capture may not be possible. Other possible device comprising with the image sensor device, located close proximity but outside of the cabinet and/or gathering the information from the bottle and/or outside of the bottle (not shown here). In another embodiment, the sensor 975 is located on the top of the cap 905, in order to increase the amount of information captured at all times. The sensor 975 can capture image of the patient as they move the bottle in order to determine whether they are taking their prescribed treatment. In FIGS. 9A and 9B, the sensor 975 is shown to be attached with the bottle, where the sensor itself can be attached in order to properly expose the device to light. In FIGS. 9C and 9D the sensor 975 can be come with focusing lens (not in details shown) and placed over the structure, as detailed in FIGS. 9A and 9B in order to have more easily capture optical information.

Figures 10A, 10B:
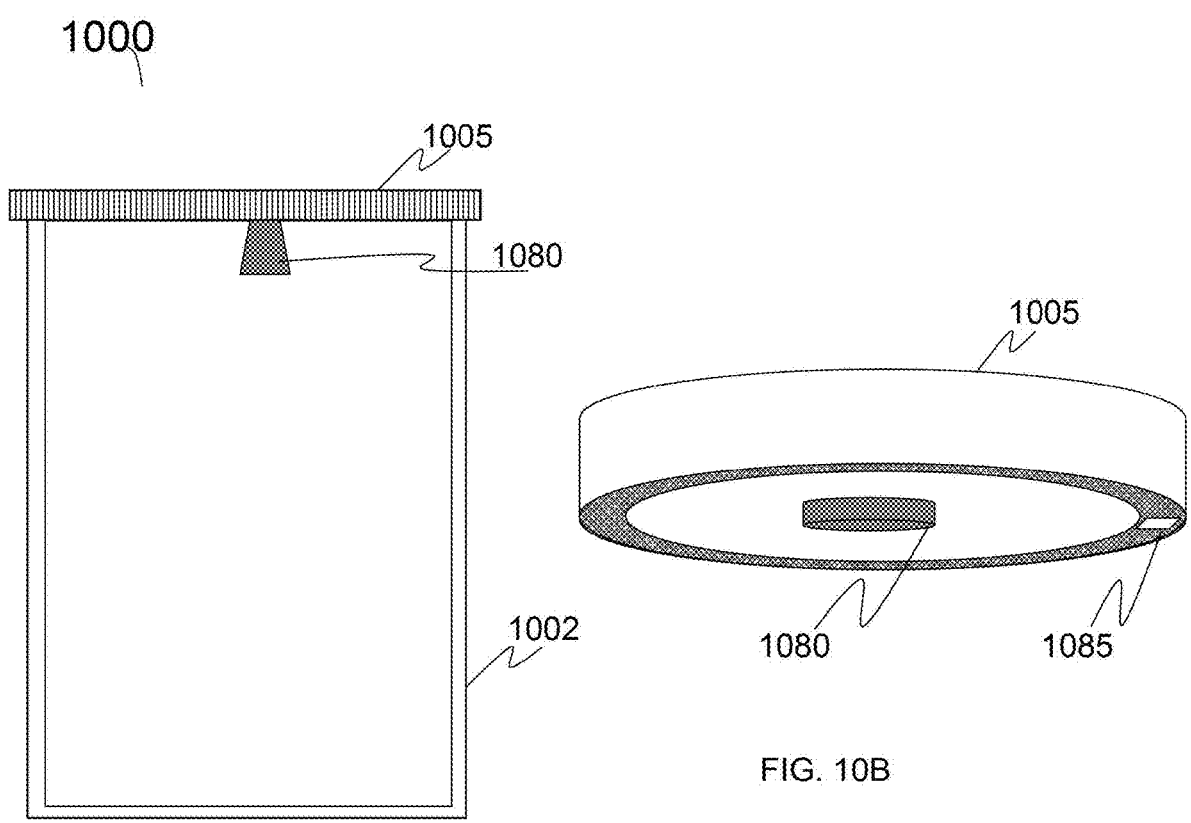
FIG. 10A is an alternate embodiment of a bottle in where the number of remaining pills is calculated through image processing means with the use of a camera on the inside of the bottle.
FIG. 10B is a schematic showing the side view of the cap of the bottle fixed with an image sensor.

FIGS. 10A and 10B are the schematics showing the bottles and its cap, respectively, in the preferred embodiments according to this invention wherein like numeral represents the like part, therefore the repeated explanation mentioned in FIGS. 1A to 9D, are omitted here. In FIG. 10, an image processor 1080 is placed inside the bottle 1000. This processor 1080 process the signal receives from the sensor (not shown here) and relay visual information to the programmable device 1015 (not shown here) in order for it to calculate the number of pills left in the bottle. The image processing may be done on the computational devices on the bottle 1000 or through a connected device (not shown here). FIG. 10B details how captured images will be relayed through an electrical contact 1085, to the bottle 1000, which connects to the processor 1015 (not shown here). The processor 1015 process the signal and, relay this information to the user through the use of the on-bottle display, 1020 (not shown here) or through a connected device (not shown here).

Connected to Internet of Things (IoT) and or Other Devices

Figure 11A:
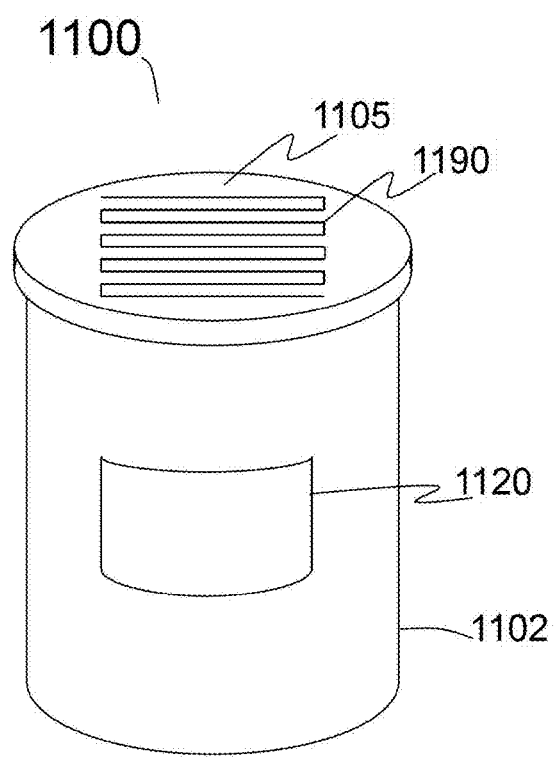
FIG. 11A is a schematic showing of a bottle with the ability to transmit, or receive or both data through the use of an antenna, located at the top of the bottle.
Figure 11B:
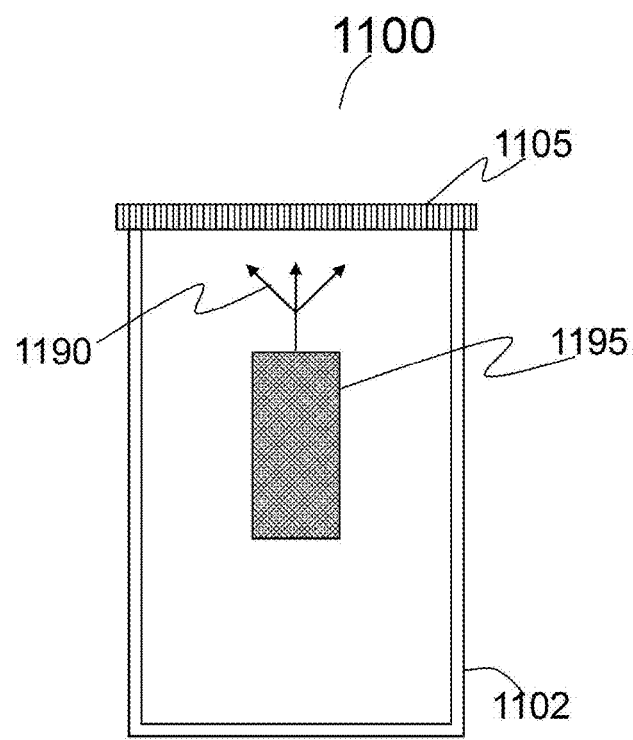
FIG. 11B is a schematic showing of an alternate embodiment of a bottle with the ability to transmit, or receive or both data through the use of an antenna, mounted at the side of the bottle.

FIGS. 11A and 11B are the schematics showing the bottles, in the preferred embodiments according to this invention wherein like numeral represents the like part, therefore the repeated explanation mentioned in FIGS. 1A to 10B, are omitted here. FIG. 11A illustrates an embodiment wherein the bottle 1100 further comprises an antenna and a receiver 1190 allowing the device to communicate with other wireless connected devices. Furthermore, the antenna 1190 may allow all previously mentioned embodiments of the bottle to connect to wireless networks (home and/or public/private networks) and exchange information with communication devices, located in close proximity and/or distant via wireless network. The antenna 1190 in the bottle may be of a variety of designs, such as but not limited to wire, PCB, chip, with subsets such as micro strip, inverted F, NFC, or Bluetooth. The antennas may be able to only transmit or receive data, or may be capable of both transmitting and receiving information from or to an outside communication device. FIG. 11B details how the antenna 1190 may be mounted on the side of the bottle and connected to other component such as display 1195, and communicates with a communication device (e.g. cellular receiver and/or transmitter). The addition of an antenna allows several possibilities that are explained in embodiments below.

Figure 11C:
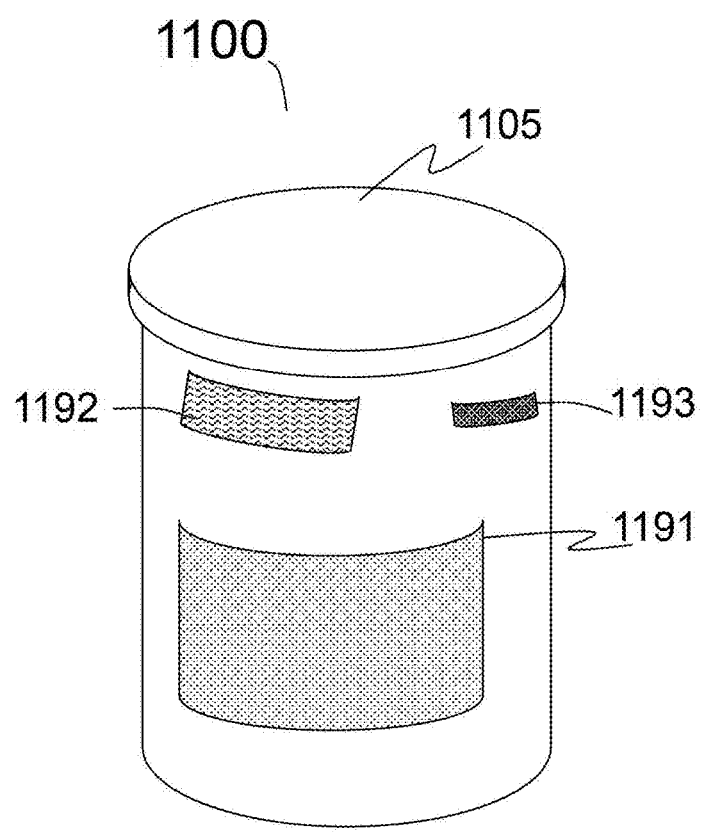
FIG. 11C is a schematic showing of an alternate embodiment of a bottle with the ability to transmit, or receive or both data through the use of a RFID, mounted at the side of the bottle.

In an alternative embodiment, as shown in FIG. 11C, the bottle system has a RFID device 1191 which can be transmitter, receiver, or transmitter and receiver. The RFID device 1191 can send the bottle information to the receiver located close proximate location to the bottle and/or carried by the patient/user. In another embodiment, the RFID device 1191 can able to locate or map the patient and/or the bottle location. In another preferred embodiment, the bottle can have a speaker 1192 to convey the alert, notification, display information (as mentioned in earlier) or combination thereof through audio message. The RFID device 1191 on the bottle or close proximity can able to show its current location on a communication device (e.g. a smart phone). This will help the patient find his or her medication, whenever they lose track of it. In close proximity, the patient can directly pinpoint the location of the medication by pressing a button on the application which will cause the medication container to create a ping (not shown here). With the pinging sound, the patient or a caregiver will be able to locate his or her medication. In another embodiment, further additional a bright flashing light on the bottle will visually help the patient or caregiver to find the pill container.

IoT Connection

When the bottle is connected to a wireless network there are numerous embodiments for alerting the patient to take their medication. One of the possible methods as an example is via text message.

Figure 12A:
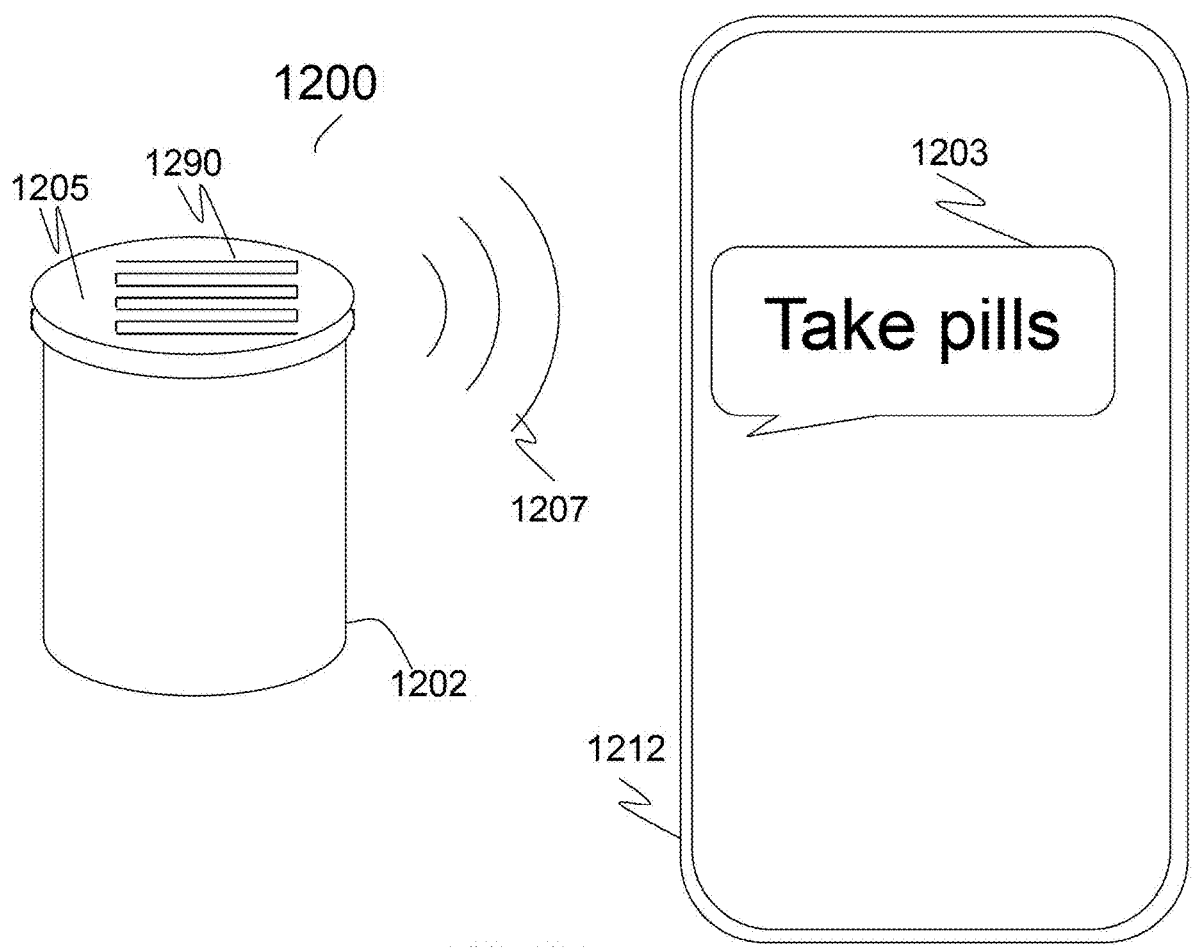
FIG. 12A a schematic showing a system showing a way how the information from the antenna may be transmitted to the electronics means located in close proximity making a closed system using communication means such as home intranet
Figure 12B:
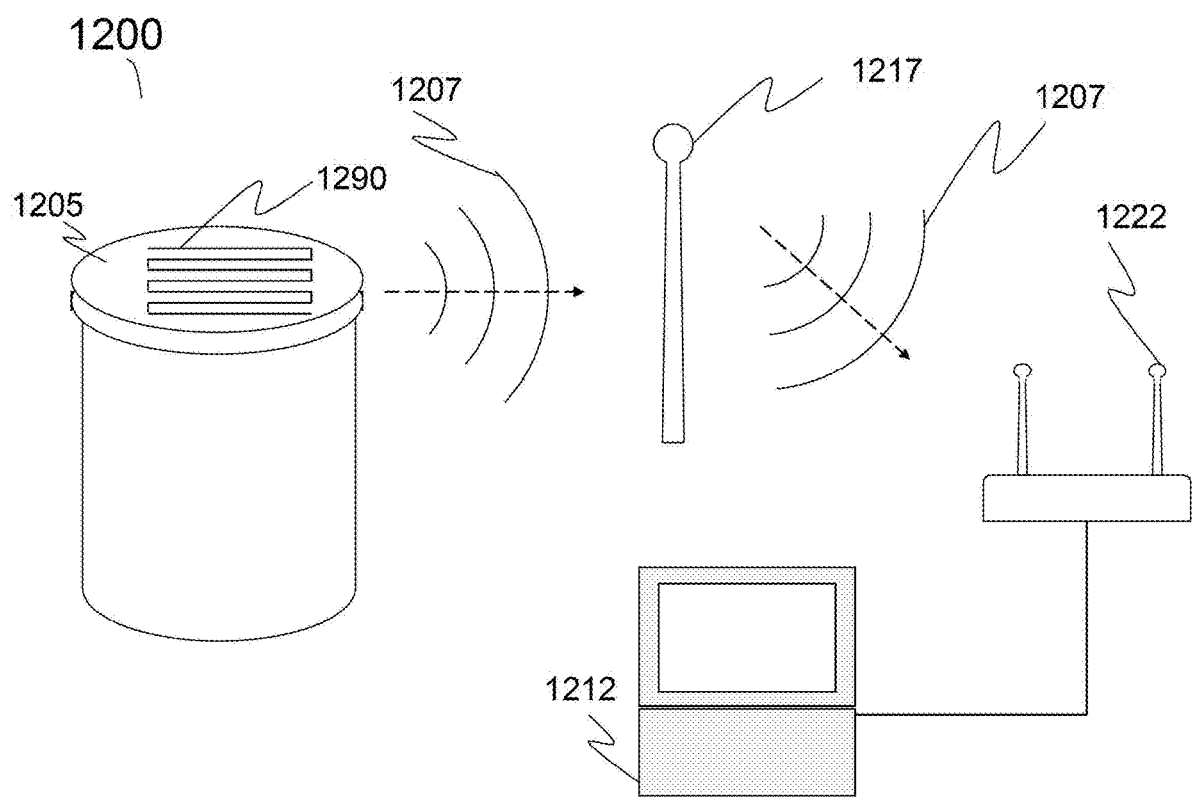
FIG. 12B is a schematic showing an alternate embodiment of a system where the bottle transmits to a transmitter/receiver means which transmit/receive the information to the communication means via home intranet.
Figure 12C:
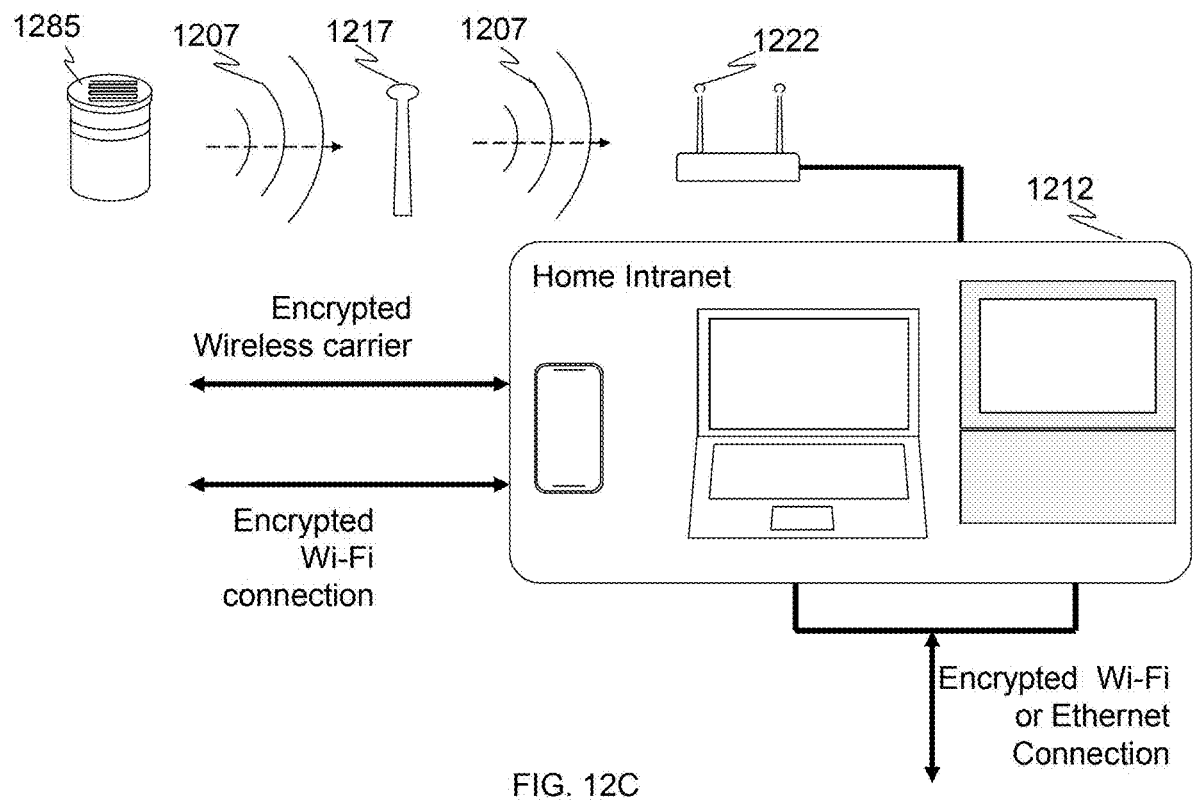
FIG. 12C is a schematic showing an alternate embodiment of a system wherein the bottle communicate with outside communication means located at the distant by using communication means located in close proximity within home network and subscribed or unsubscribed private/public networks.

FIGS. 12A to 12C are the schematics showing various alternative embodiments of a system comprising of bottle, communication device, and networks, according to this invention, wherein like numeral represents the like part, therefore the repeated explanation mentioned in FIGS. 1A to 11B, are omitted here. FIG. 12A shows an example of message variant that bottle can send the data to communication device (i.e. smart device 1212), in the preferred embodiment according to this invention, wherein like numeral represents the like part, therefore the repeated explanation mentioned in FIGS. 1A to 11B, are omitted here. The bottle n this embodiment, comprises previous elements, microprocessor, display, etc are included, but not shown. In FIG. 12A, details of a bottle 1200, its connectivity to a communication device 1212 through wireless/wired by sending the wireless signals 1207, and its conveyed information and displayed as text message 1203 as an example. The means of messaging can be done either through the internet, via IoT devices and/or have its own means of utilizing cellular networks, that sends a message to the user's communication device (e.g. phone). The message 1203 can be either be a text message, notification through any graphical user interface based application either build specifically for this application to convey the message and application capable of sending messages. This specific application (a.k.a. app) that may be pared with the bottle, an email, or other form of contact to the patient.

The messages 1203 can be conveyed to various points. This system may function within a certain period of time after the patient has missed their scheduled dose, or may be a reminder, prior to the time, depending on the patients' needs and/or preferences. The message may be custom built to the client depending on whether or what the dose was, medication, antibiotic, vitamin, or other supplement. In some instances, the text message may remind the patient that they need to take the medication, or that they have missed and/or need to take the medication latter in the day. This is situational and is dependent on the patient and the type of medication, if the patient needs to take the medication in a certain time frame, or if the patient will be adversely affected for missing a dose or several doses. In that case, the message may be sent immediately, or may be sent after missing several doses. The system may further detect when the medication has not been taken but allow time for the patient to take the medication late, allowing the patient time to be delinquent in taking the medication without being sent the messages.

Alternatively the transmitter 1290 may send data at the time when and if patient took their medication, specially to a family member, caregiver, or doctor in order for a third person to aid the patient in taking their medication. This system is useful in an instance information transmission, wherein the patient is living alone, however may need assistance from time to time. This system may be used in conduction with a home caretaker, caregiver, or other form of assisted living.

Optionally, the system may send data regarding the taking of the medication and the remaining stock of the medication to the pharmacy that supplies the medication in order for the pharmacy to be better able to stock and refill the prescription. Data sent to a pharmacy may also be used to identify miss taken medication or medication taken at too fast a rate. This rate tracking may also be useful in order to combat pain medication abuse, as pills taken too quickly will alert pharmacists and physicians that something is amiss.

Alternatively, the transmitter may communicate through the internet or wireless network to a prescription manager that tracks the patient's medications and helps the patient know when to take all of their medication. The prescription manager may be an application on a wireless device or a specified device that is in direct communication with the bottles that uses an algorithm in order to properly fulfill each patient's needs. This will be done by having all of the medications prescription/schedules which may be a part of a prescription information, stored on the prescription manager and having the prescription manager, while in communication with the bottle, transmit to the bottle when the medication is to be taken, and to contract the patient when the medication is to be taken. The prescription manager may take the place of the programmable device on the bottle or supplement the programmable device on the bottle.

In an alternative embodiment, the bottle comprises, a bottle, a cap, an energy harvester, a display, a programmable device, a sensor, a transmitter/receiver seen in FIG. 12A to 12B, a separate prescription manager, fitness manager, or other system for storing medical data. In FIG. 12A, the bottle communicates directly to a smart device. In another embodiment as shown in FIG. 12B, the bottle 1200 can connect to a proprietary/standard/(or built for this application) receiver transmitter, or combination thereof 1217 and transmit/received the data to a communication device (e.g. smart phone) 1212 through a private network (e.g. home network) through wireless signals 1207 to/from the transmitter/receiver 1217 which further has connectivity to the internet transmitting/receiving the data to distant communication device over the internet (not shown here). The communication device 1212 comprise of antenna 1222 which transmit/receive the signal 1207 to/from the transmitter/receiver/transceiver 1217, or a transponder. In alternative embodiment as shown in FIG. 12C, the communication device 1212 with app (not shown here), connected to private network (e.g. home network) can have the capability of encryption and decryption capability while transmitting/receiving the data to/from the internet, or private network, or combination thereof.

Figure 13A:
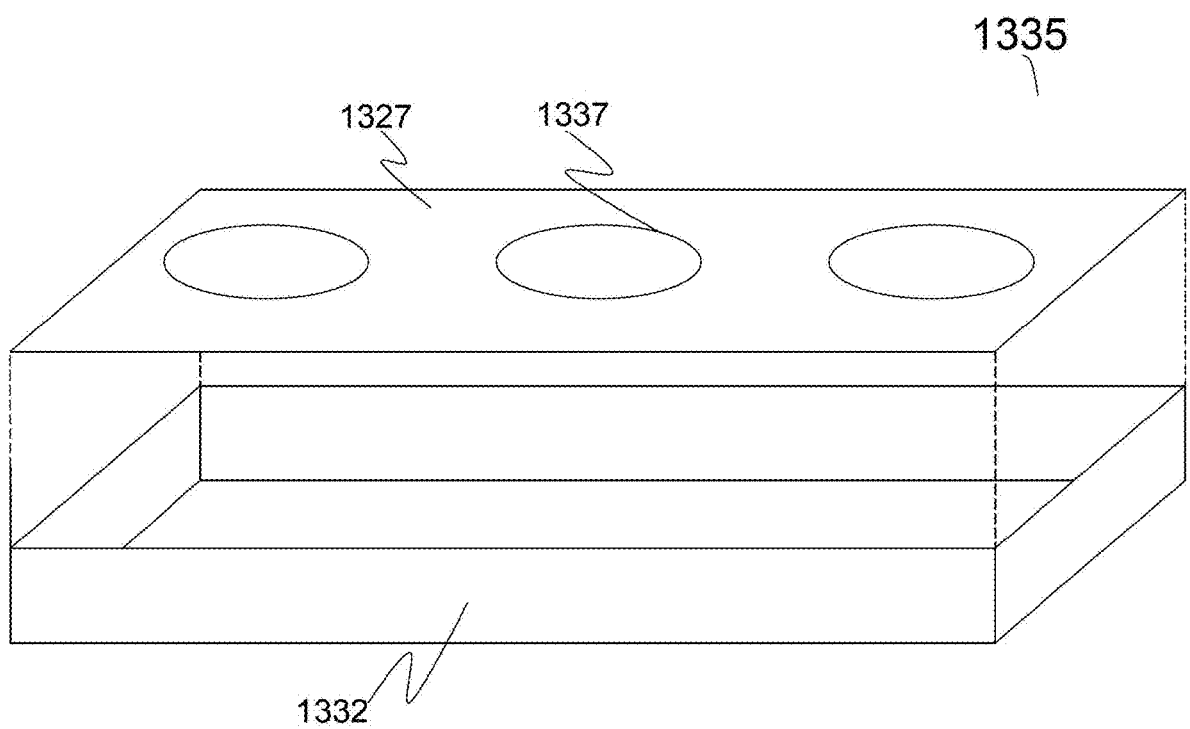
FIG. 13A is a schematic of a caddy/carrier which may power the bottles and/or act as an intermediary between the bottle and other computational equipment in the preferred embodiment.

FIGS. 13A to 13D are the schematics showing various views and various embodiments of caddy or carrier which can carry single or multiple bottles in the preferred embodiment according to this invention, wherein like numeral represents the like part, therefore the repeated explanation mentioned in FIGS. 1A to 12C, are omitted here. In the preferred embodiment, as for example not for limitation, the caddy (or carrier) comprises of multiple opening 1337, which have contacts (not shown here) at the bottom 1332 to provide the bottles with power and communication to other devices through the caddy's transmitter and receiver (not shown here). FIG. 13A is the schematic showing the caddy/carrier itself according to this invention. The caddy 1335 comprises a top 1327, a hole to hold/place bottle (not shown here) 1337, a bottom 1332 with electrical contact (not shown here).

Figure 13B:
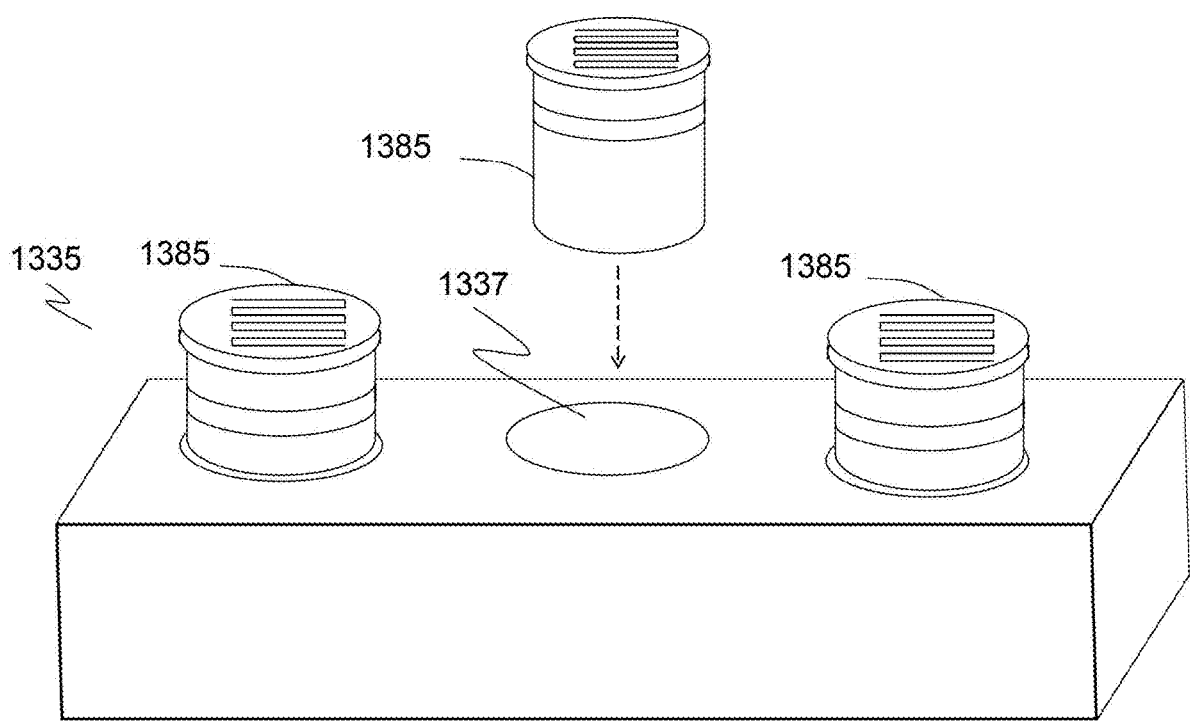
FIG. 13B is a schematic of an alternate embodiment of a caddy/carrier's showing three bottles and their interaction with the caddy/carrier.
Figure 13C:
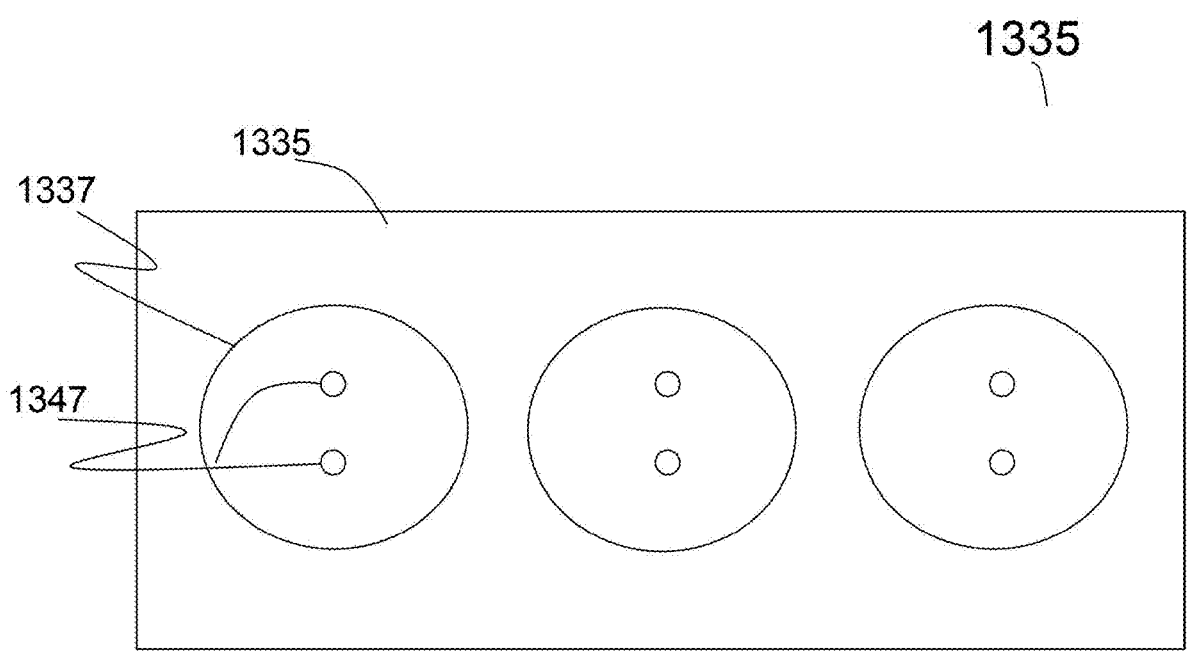
FIG. 13C is a schematic showing a top view of the caddy/carrier wherein, the slots for the bottles and contacts which may be used for either charging and/or communicating from the bottles to a communication means.
Figure 13D:
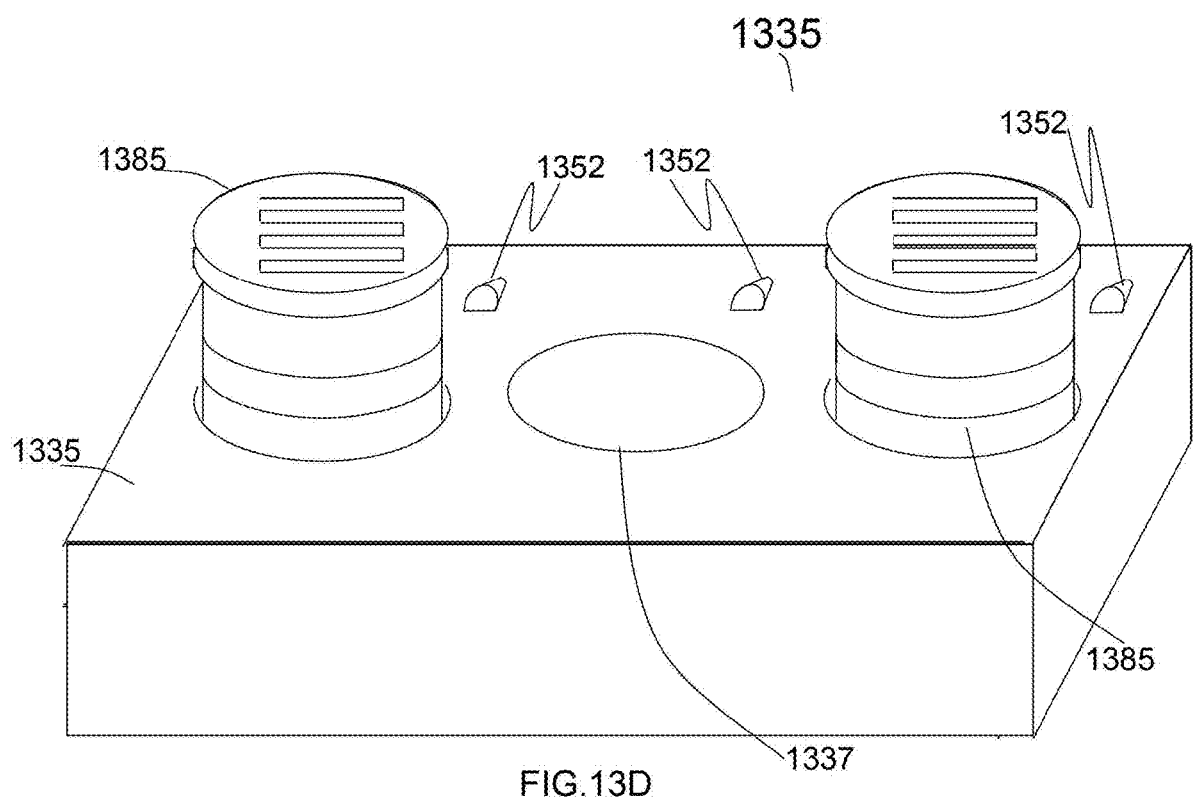
FIG. 13D is a schematic showing a alternate embodiment of a of caddy/carrier which tracks both the remaining pills and the action of taking the pill using cameras located on the caddy/carrier.

FIG. 13B is a schematic showing the side view of a caddy with the bottles, in the preferred embodiment according to this invention. FIG. 13B also shows how the bottles 1385 is to be placed and, and caddy 1335 works in together. The bottles 1385 as shown in FIG. 13B are placed into slots 1337, where the bottles 1385 may be powered and/or communicate with the carrier 1342, through electrical contacts (not shown here). FIG. 13C is a schematic, showing top-view of the caddy/carrier 1335, with the contacts 1347, clearly shown at the bottom of the slot 1337 (e.g. 1337a, 1337b, and 1337c). In FIG. 13D, the caddy 1335 has a single or multiple image sensors 1352 located on the top of the caddy and may or may not connect to each slot 1337. Just for an example, but not for the limitation, the caddy has 3 small cameras 1352, which monitor the bottles in a similar fashion to the image sensor electrically connected to the bottle mentioned in FIG. 13C. These cameras 1352 are connected to and powered by the caddy 1335. The caddy 1342 houses batteries and/or energy harvesters (not shown here) in order to power the bottles as well as transmitters and receivers (not shown here). These communication devices may act as the wireless receiver detailed in the FIGS. 12A to 12C and are connected to the internet. The function of the device begins when a signal is received from bottle and process the signal and sends appropriately as described earlier.

Figure 14A:
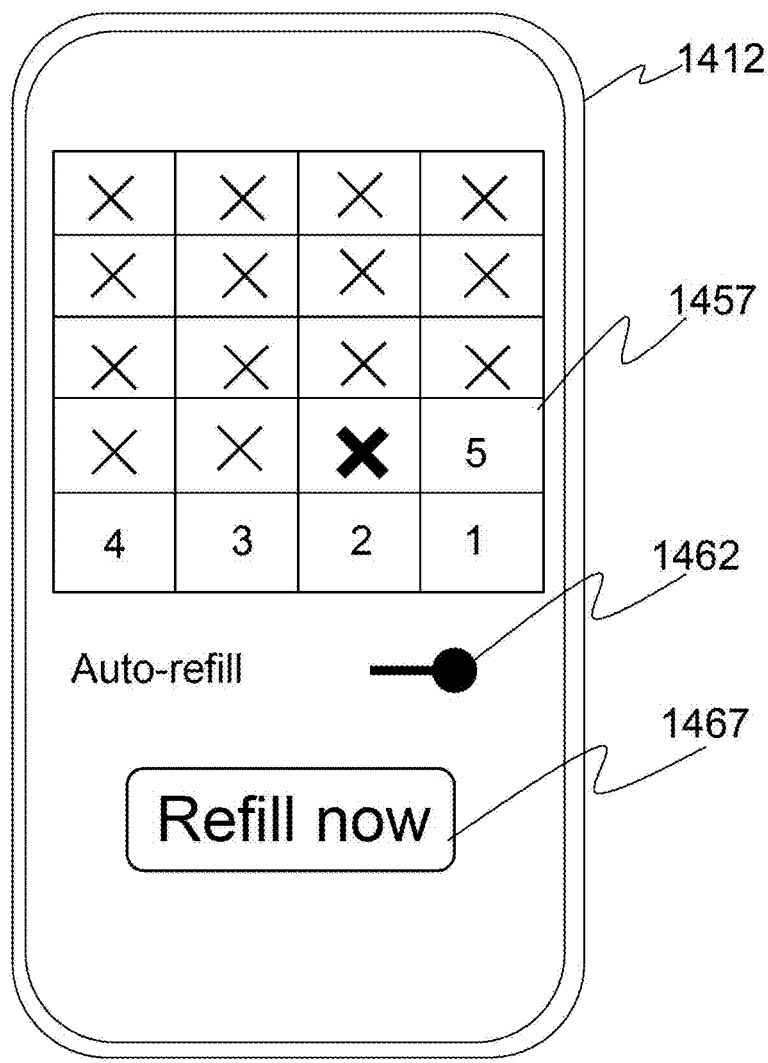
FIG. 14A is a schematic showing a display an example of an application showing the data to manage the prescription, through a communication device and/or for display the bottle information in display unit itself in the preferred embodiment.

FIG. 14A is a schematic, showing an example of display which shows the information of bottle based don the application on a communication device (e.g. phone) 1412, in the preferred embodiment according to this invention. This prescription/fitness manager manages and recodes when a prescription, vitamin, medicine or supplement has been taken by the client. The prescription/fitness manager communicates to the bottle wherein the display shows when the next dose is to be taken. The prescription manager either has a display, or is able to be accessed through a smart device (communication device) such as a cell phone, or other internet accessible device, allowing the client to see all of the patient's prescriptions, vitamins, supplements or medications that the client needs to take and when to take them.

Figure 14B:
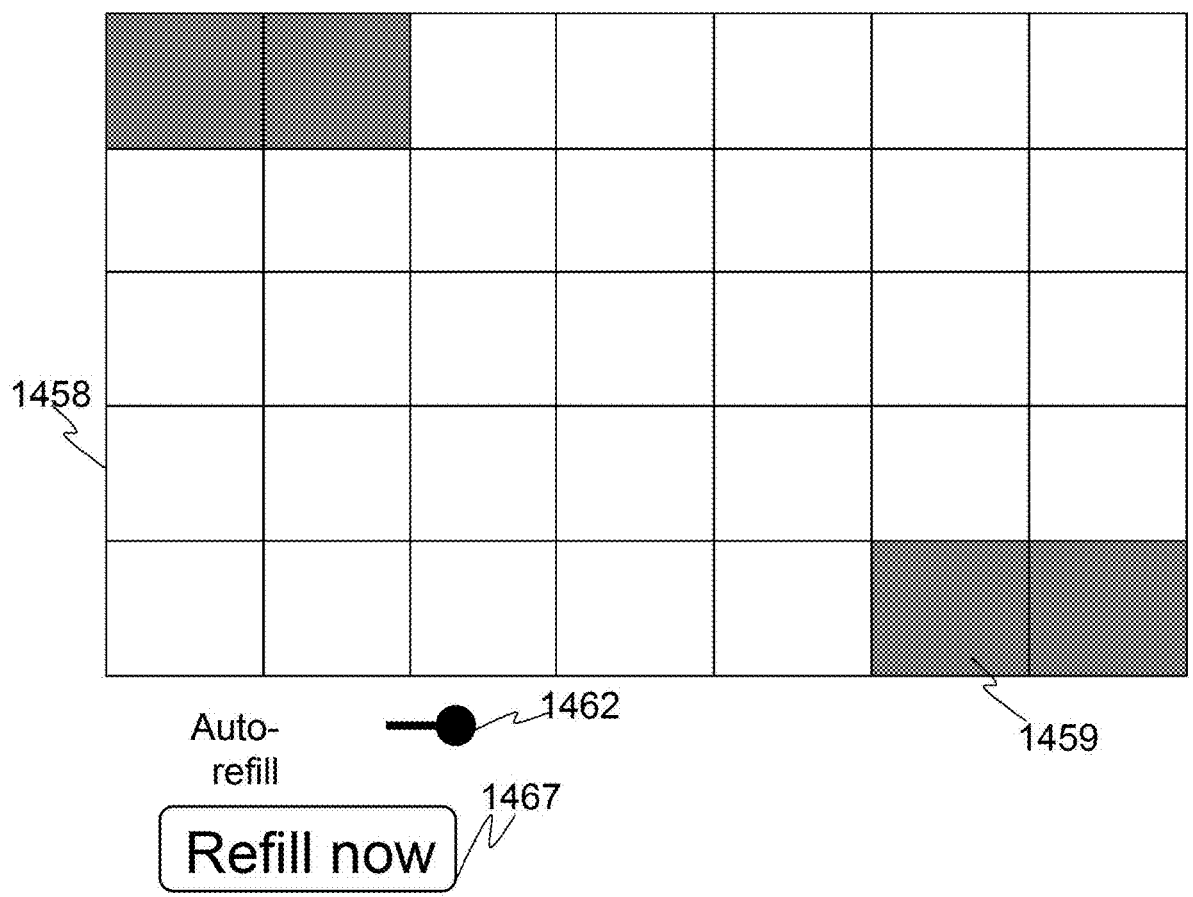
FIG. 14B shows a schematic displaying an example of an application which can use data from the bottle to manage the prescription by using of communication means (e.g, here on a personal computer).

Alternatively and/or also optionally, the display may have a calendar style display 1457, as shown in FIG. 4A, and the grid corresponds to a calendar with the "x's" represent a dose that has been taken, and the bold "x" representing the current day. The numbers on the display are meant to convey the number of pills left. Below the calendar is the option to have the manager auto refill reorder, noted here as 1462, the treatment for the patient, and further below of that is a button where the patient can optionally push the button to refill the medication now 1467. FIG. 14B shows an alternative embodiment of display calendar wherein the similar numeral represents the like part as explained in FIG. 14A, so that repeated explanation is omitted here. In FIG. 14B, the difference is that the display calendar 1458 in FIG. 14B comprise of dates with empty space with date (not shown here) on which the medication was taken, and the dark space 1459 of the date chart represents the date on which the medication is to be taken or left to be taken.

For example, but not to serve as a limitation the bottle system itself will only sense when the bottle is opened, and send the data to the manager, and receive the time of the next dose. The prescription/fitness manager is either by itself programmable, or is programmable through a connection with a wireless device, such as a smart phone. The only data that needs to be inputted is the dates and times for the prescriptions and whether and when the prescription was taken.

Alternatively, the prescription manager may be programmed by the doctor's office or pharmacy, and may automatically be updated by the doctor's office or pharmacy when new prescriptions are prescribed or filled. Optionally the pharmacy may update the prescription manager when vitamins or supplements are purchased, as well as when over the counter medicine is purchased, such as cold medicine. Optionally the prescription manager is viewable to the doctor, pharmacist office, or caregiver of the patent to ensure that the medication is being taken as prescribed. This invention allows the pharmacy to better anticipate when the client will require a refill and/or require to update the prescription information.

Figure 15A:
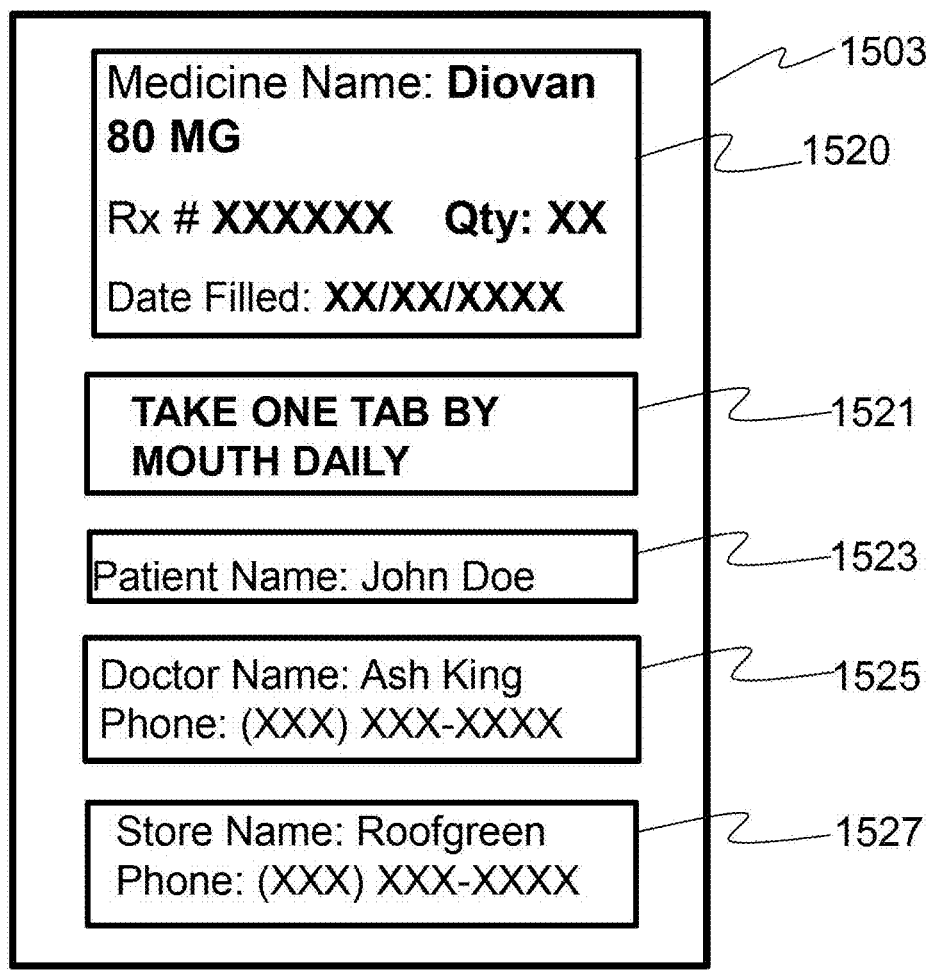
FIG. 15A shows a graphical view of an administrator (pharmacy) screen display of the smart medicine Intake system in the preferred embodiment.
Figure 15B:
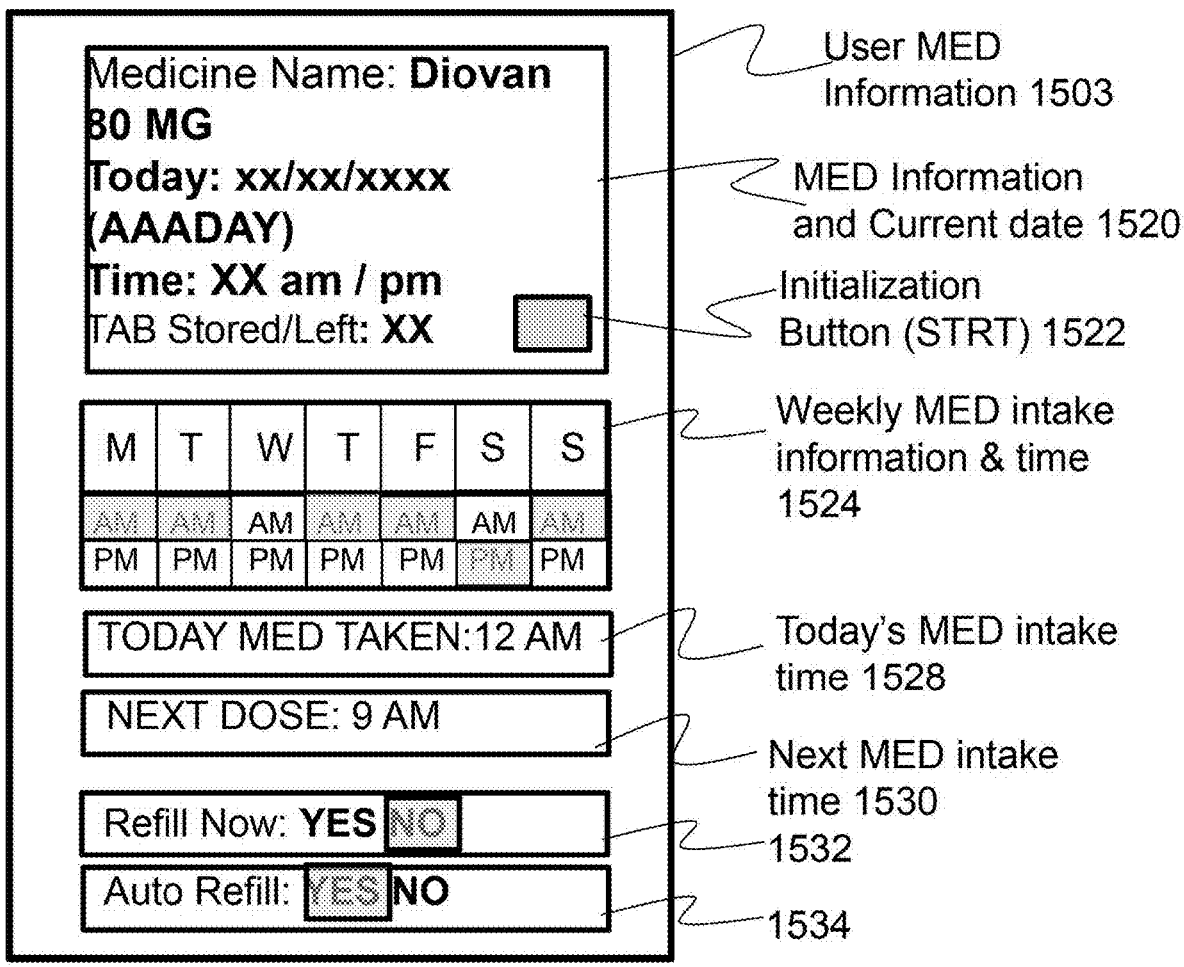
FIG. 15B shows an alternate embodiment of a graphical view of a view of a user/patient screen display for the smart medicine Intake system in the preferred embodiment.

FIGS. 15A and 15B are the graphical views of an administrator screen display and user/patient screen display in the preferred embodiment, according to this invention wherein similar numerals represent the like part as explained in FIGS. 13A to 14B so that repeated explanation is omitted here. The sensor information especially information on the MED taken or/not, its date and time are shown in only FIGS. 15A and 15B, as an example. The sensors (not shown here) can be coupled to the user interface with an internal communication path (not shown here) and can deliver the information to the user interface to show the information in the display. The user interface is contemplated to be a display screen/screens (such as 1520, 1521, 1523, 1525, and 1527 in FIG. 15A), an interactive display screen, speakers, and/or a combination thereof. Single and/or multiple sensors as shown in FIG. 1 to FIG. 12 which can detect when a user/patient takeout the MED and date and time and create the MED left. The information can be stored, transmit through antenna attached with it, or combination thereof to the communication means either directly and/or via to the additional sensor located in proximate distance to the bottle or carrier. The user interface (not shown here) can further provide feedback to the user/patient regarding whether or not the user/patient is taking the medicine in prescribed time, missing the MED according to the pharmacy/doctor prescription/suggestion.

As noted earlier, but not shown here however, pill bottle and/or carrier can further include other sensor which can provide the user/patient or their distant person with feedback of the user/patient's wellness through detecting user/patient's blood-pressure, heart-rate, oxygen concentration, glucose level, facial image etc. or combination thereof, and by showing the information to the display in another mode of operation.

Referring now to FIG. 15A, therein is shown a graphical view of a screen display 1503 for the MED Intake System incorporated in Pill bottle and/or carrier. The screen display 1503 (also hereinafter mentioned as pharmacy controllable display or user MED information) can be displayed on one side of the bottle and/or the side (visible from outside) of carrier. Part of the screen display 1503 may include the MED name and its Quantity in 1520, frequency of intake 1521, Patient name 1523, and Doctor name 1525, which are shown or displayed on the display. Optionally, the store name and its contact information may also include in the display 1503 as in 1527. Pharmacy and/or Doctor Office has only access to input those data into the system. The screen display 1503, as shown in FIG. 15A, can include a header MED name and its dose level, and also may include date of filled and its MED quantity. Below the MED information level 1520, can be the information on the frequency of Med 1521 to be taken per day. Below the MED Frequency level 1521 are the Patient name 1523, Doctor Name 1525, and Pharmacy information and phone number in 1527. Various ways, the administrator display can be designed, in which only pharmacy and/or doctor office has the access to input the requite data for MED, patient, Doctor, store, or combination thereof. It is contemplated that the MED information could be input directly to the bottle and/or carrier, or could be sent to the distant located bottle and/or carrier via Radio and/or internet using the public/private network.

The bottle and/or carrier further comprises of the time meter (not shown here) that can correspond to the time counting after refilling and/or input the MED information, to first MED is taken. If the time between Refilling to MED taken is passed certain period (which is also only input by the administrator), bottle will show the signal in the display and/or started to send the information to the Pharmacy and/or Doctor office or distant person to indicate that the MED is not taken but refilled and delivered. For example, if the MED system is configured to require to take the MED within 48 hours after refilling, then as soon as the time meter reach to 48 hrs, it automatically starts to send the signal to bottle and/or carrier located at the user/patient home/place to show the alert in the display. Further, in simultaneous, it is also contemplated that the signal of alert can also be sent to the communication means of the designated person (i.e. close relative). This will provide additional advantages to remind the patient/user/designated person remotely to take the MED.

Referring now to FIG. 15B therein is shown a graphical view of a view of alternative embodiment of user/patient screen display 1503 for the MED Intake System incorporated in Pill bottle and/or carrier. The user/patient screen display 1503 can be displayed side by side to the pharmacy controllable display (mentioned earlier) or other side (opposite side of pharmacy controllable screen) of on one side of the bottle and/or the side (visible from outside) of carrier.

The user/patient screen display 1503 can include a header (may located at the top) 1520 that includes a MED name and its doses, today's date and time (in AM/PM), TAB stored or left in XX (herein after also mentioned as counting meter) in quantity. Further, it may also include the initialization button 1522, which may need to push while starting to take the MED. As an illustrative example, the title can be "STRT".

Below the user/patient MED information, the header 1520, weekly MED intake history 1524 is located. It is contemplated that weekly time meter in AM/PM 1526 indicates that when the MED was taken in a day. The shaded area in 1526 indicates the MED taken. For example, if the MED is supposed to take in 9 AM, the user/patient takes around (+/−15 min period), AM is shown in color coded. There is a chance that the user/patient may not able to take the MED within the specified time period (+/−15 min) from 9 AM, and if the user/patient takes the medicine other time but in AM (before 11:59 AM), the same AM may show up in Red or other coded different from the previous color coded wherein the Med is taken within the specified time period from 9 AM. It is also contemplated that the user/patient may take the MED not in AM but in PM, then the color PM is shown (in the day) with other color coded. It is also contemplated that user/patient may forget taking the MED on the DAY, in that case AM or PM will not be shaded and color coded. Further, the screen may include the portion (not shown here) showing the skipped and the date.

Below the weekly history screen 1524 and 1526, is an exact time screen 1528, indicates when the MED is taken in the day. The exact time meter 1528 can include a minimum compliance time indicator to take the MED, and a highest compliance time indicator, in between of which the MED requires to take (not shown here).

Below to the exact time screen 1528, is a time screen 1530, indicates when the time to take the next MED and possibly may include also the date/week (not shown here). The user/patient screen 1503 may also include the Refill option 1532 and Auto Refill option 1534 screens, one after another but below the time screen 1530.

It is contemplated that the counting meter as shown in 1522 to 1530 can indicates quantities remains in the bottle, and the quintiles is measured from the sensor signals, and post-processing the data. The Refill Now button gets lighted when specified quintiles remains in the bottle. For example, the specified MED quantities can dependent on the quintiles to be taken in the specified days (e.g. 5 days), when that quintiles reach, automatically Refill Now button gets lighted for user/patient to know to call to the Pharmacy. It may include the button/screen to send the information to Pharmacy; if not auto refill is not chosen.

It is to be noted here that FIGS. 15A and 15B shows only for the case of pills or tablet cases as examples, however, similar display screen can also be implemented for the liquid MED and also incorporated with options of TAB MED or Liquid MED as a selection, initially to be selected by Pharmacy or Doctor office.

Figure 16A:
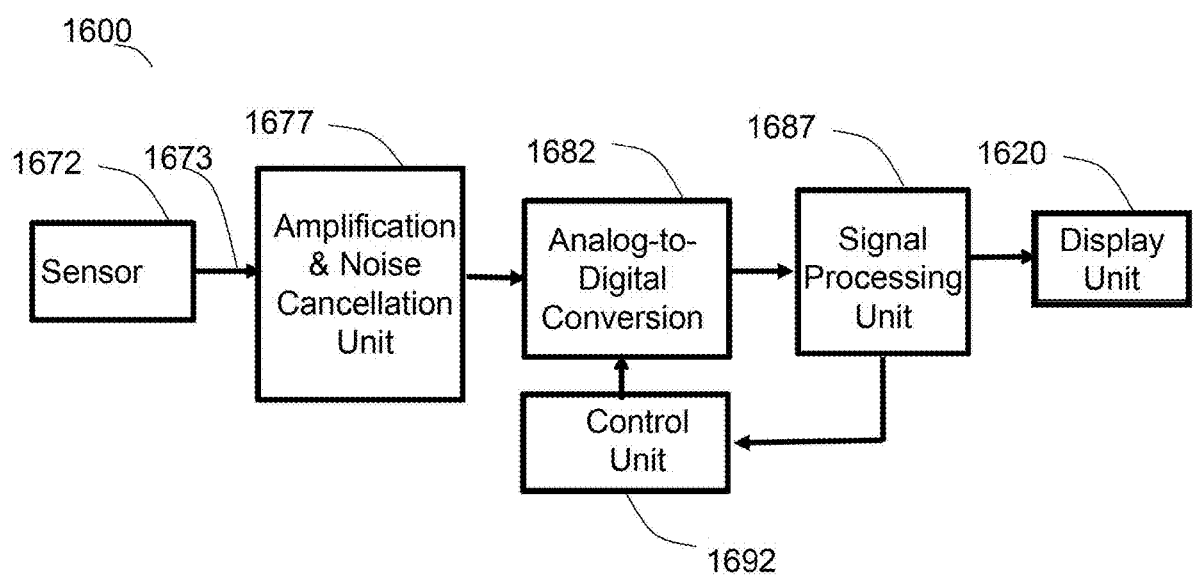
FIG. 16A shows the schematics showing the block diagrams of a system based on which the majority of the embodiments described earlier are operated.
Figure 16B:
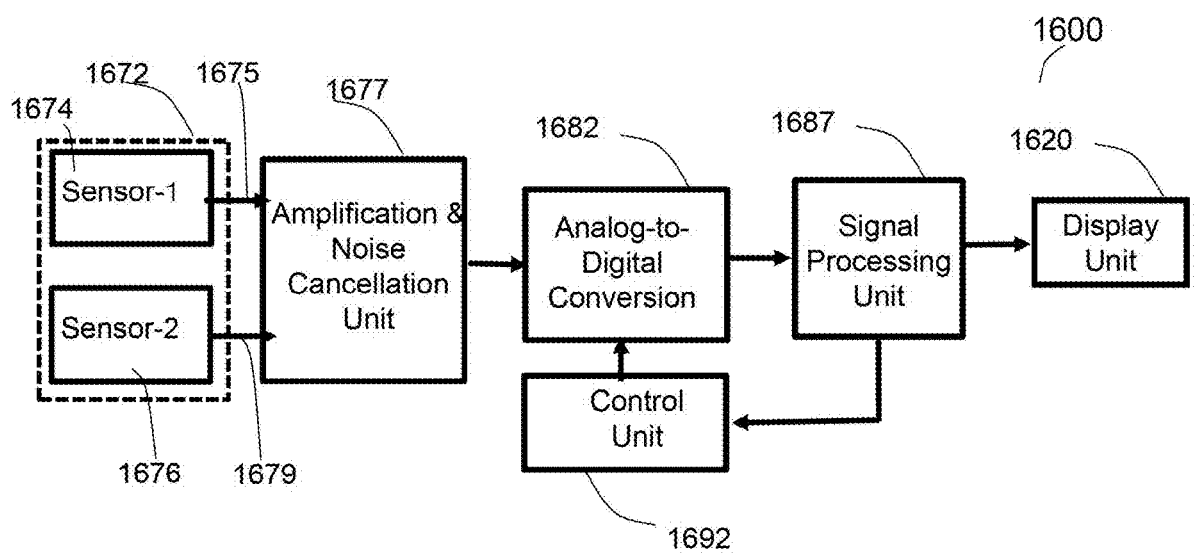
FIG. 16B is the schematics showing the block diagrams of an alternate embodiment system with an additional sensor not in the FIG. 16A.
Figure 16C:
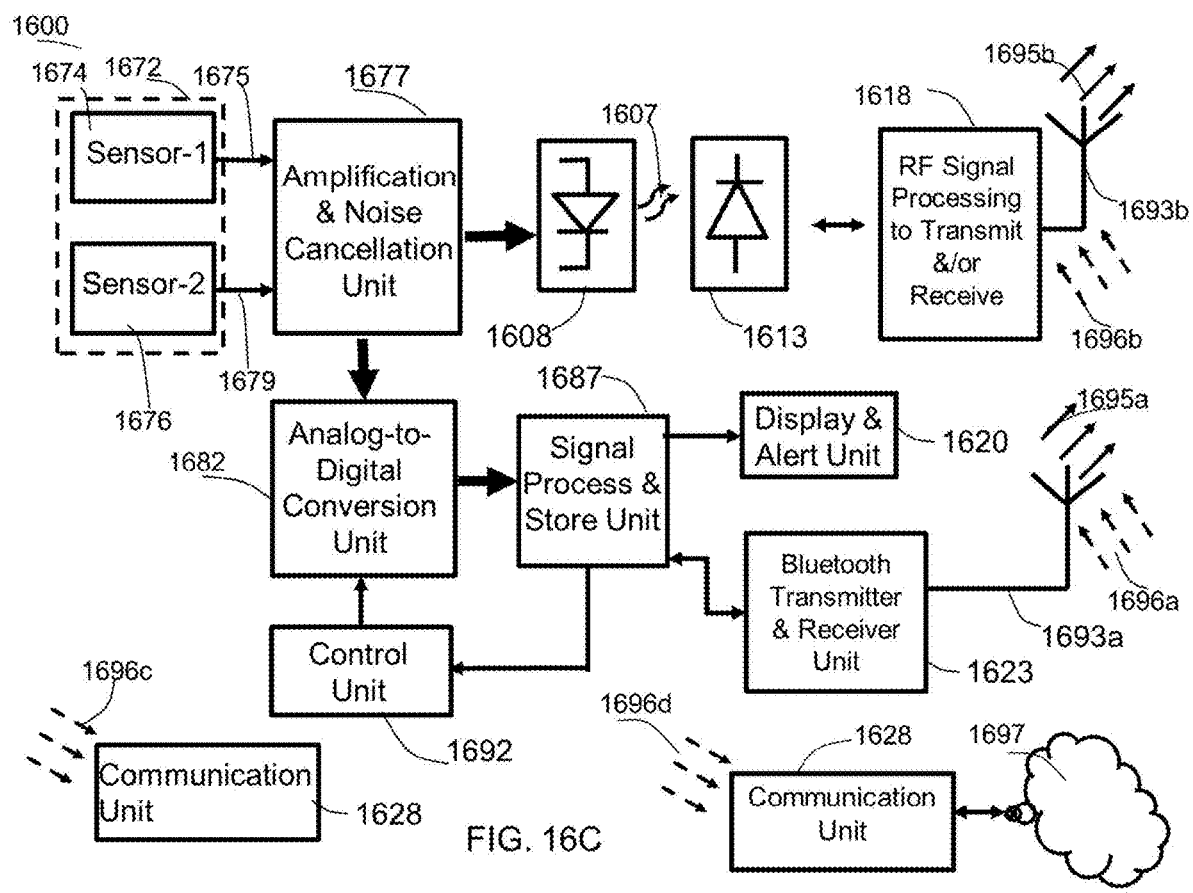
FIG. 16C is the schematics showing functionalities of bottles and its communication connectivity via a wireless and/or wired connectivity from the bottle to a home network and outside internet in the preferred embodiment.

FIGS. 16A to 16C illustrate schematics of block diagram of an exemplary functional blocks and associated functionalities of bottle operable to interact with the smart bottle system and associated functionality. In order to provide additional context for various aspects thereof, FIGS. 16A to 16C and the following discussion are intended to provide a brief, general description of a suitable environment in which the various aspects of the innovation can be implemented. While the description includes a general context of electronic means (e.g. computer or communication device) executable instructions, which can be located in the bottle, bottle system, or/and in the communication device, those skilled in the art will recognize that the innovation also can be implemented in combination with other program modules and/or as a combination of hardware and software.

FIG. 16A is a block diagrams of an exemplary of a sensor peripheral functional block operable to interact with the bottle system and associated functionality in the preferred embodiment according to this invention. In order to provide additional context for various aspects thereof, FIG. 16 and the following discussion are intended to provide a brief, general description of a suitable environment in which the various aspects of the innovation can be implemented. While the description includes a general context of functional block, those skilled in the art will recognize that the innovation also can be implemented in combination with other module block and/or as a combination of hardware and software. In order to provide additional context for various aspects thereof, FIGS. 16A to 16C and the following discussion are intended to provide a brief, general description of a suitable environment in which the various aspects of the innovation can be implemented. While the description includes a general context of functional block integrated into integrated circuit a part or whole, which can be located in the bottle or/and in the communication device, those skilled in the art will recognize that the innovation also can be implemented in combination with other module block, program modules and/or as a combination of hardware and software.

Generally, functional block and/or specific applications block (e.g., modules) can include functional blocks, components etc. that performs particular tasks simultaneously with other or separately with other functional block to create the information required to know the patient/user behavioral data or statistics of the medication intake of the patient/user. Moreover, those skilled in the art will appreciate that the inventive methods can be practiced with other system configurations, including but not limited to single-processor or multiprocessor systems, minicomputers, mainframe computers, as well as personal computers, hand-held or embedded computing devices, microprocessor-based or programmable consumer electronics, and the like, each of which can be operatively coupled to one or more associated devices.

In the block diagram input signal is generated through the sensor 1672. The sensor may be one of a variety previously listed, includes but not limited to a pressure sensor, lights, accelerometer, proximity, pulse oximeter, blood pressure sensor, or combination thereof. The sensor 1672 will receive power from the power circuitry (not shown here) and sends the signal 1673 to the amplifier unit 1677, wherein the signal 1673 is amplified from the level captured by the sensor. Amplification can be done through a variety of means, including, but not limited to, low noise (LNAs), variable gain amplifiers (VGAs), and/or other amplification systems and circuitry. Noise cancellation may take place within the amplification or before or after through the use of other subsystems and circuitry. The noise cancellation may be done through feedback loops, filters in analog domain and that follows the conversion of analog to digital in analog-to-digital unit 1682 (hereafter mentioned as ADC). The ADC 1682 will have a wide range of specifications, largely dependent on the type of sensor and resolution sought after. Again, like the other components listed, power can be supplied either using the battery, power supplies, power drawn from the energy harvester, or combination thereof, and if need be from the energy storage device. The ADC will have three total connections, first is that to the amplification circuitry, next to the signal procession unit 1687 and last to the control unit 1692. In the signal processing unit 1687 the signal in conditioned and corrected, by the need of the device at the time. The signal processing unit 1687 comprises of a digital signal processor, a central processing unit, microcontroller unit or any combination thereof. In the processing unit 1687 the signal is analyzed, updates memory, and sends the information processed to the display. The control unit 1692 is connected to the ADC 1682 and controls how the signal incoming from the amplification stage is digitally filtered and the sample rate. The processing unit is also electrically connected to the display 1620 and sends the appropriate signals depending on the display type.

FIG. 16B are the block diagrams showing an alternative embodiment of the sensor peripherals functional blocks, according to this invention wherein similar numeral represent the like part as shown in FIG. 16A, therefore, the repeated explanation is omitted here. In FIG. 16B, the sensor system comprises of multiple sensors 1674, and 1676 and this system 1600 has the ability to process more than one sensor's in put at a time. In FIG. 16B, sensor system 1672 comprises of more than one sensor which are shown to function in parallel. In the block diagrams as shown in FIG. 16B, input signals 1675 and 1679 are generated by the sensor system 1672. The sensor may be one of a variety previously listed, including, but not limited to a pressure sensor, lights, accelerometer, proximity, pulse oximeter and/or blood pressure sensor. The sensor system 1672 receives power from the power circuitry (not shown here). The sensor signals 1675 and 1679 from sensor system fed to the amplifying unit 1677 to amplify the signal from the level captured/generated by the sensor. Amplification can be done through a variety of means, such as but not limited to, low noise (LNAs), variable gain amplifiers (VGAs), and/or other amplification systems and circuitry. Noise cancellation may take place within the amplification or before or after through the use of other subsystems and circuitry. The noise cancellation may be done through feedback loops, filters in analog domain and that follows the conversion of analog to digital in analog-to-digital unit 1682 (hereafter mentioned as ADC). The ADC unit 1682 has a wide range of specifications, largely dependent on the type of sensor and resolution sought after. For detecting small signal, the ADC can be designed to have high dynamic range, wherein dynamic range is defined as the ratio of large signal sense to smallest signal sense. Again, like the other components listed, power can be supplied either using the battery, power supplies, power drawn from the energy harvester, or combination thereof (not shown here). The ADC unit 1682 will have multiple connections first is that to the amplification circuitry 1677, next to the signal procession unit 1687, and last to the control unit 1692. In the signal processing unit 1687 the signal in conditioned and corrected, by the need of the device at the time and process the signal and provide the output readable by the patient. The signal processing unit 1687 comprises of a digital signal processor, a central processing unit, microcontroller unit, memory or any combination thereof. In the processing unit 1687 the signal is analyzed, updates and stored in memory and sends the processed information to the display 1620. The control unit 1692 is connected to the ADC 1682 and controls how the signal incoming from the amplification stage is digitally filtered and the sample rate. The processing unit 1682 is electrically connected to the display 1620 and sends the appropriate signals depending on the display type. Optionally, the display is connected to interface unit (not shown here) and input the data which could stored in the memory as the reference data, and/or recall the data which was stored while taking the medication at the certain period of time.

FIG. 16C are the block diagrams showing the sensor system in the preferred embodiment according to this invention wherein the similar numeral represents the like part as shown in FIGS. 16A and 16B, therefore the repeated explanation is omitted here. In FIG. 16C, the details connectivity of bottle system is shown as an example, but not for limitation. The bottle system 1604 comprises of a bottle (not show here), sensor unit 1672, amplification unit 1677, ADC unit 1682, signal processing unit 1687, electro-optic system 1608 and 1613, RF transmitter/receiver unit 1618, Display unit 1620 connecting to the signal processing unit 1687, Bluetooth unit 1623, communication unit 1628, and antenna 1693a (and 1693b) for transmitting signal 1695a (and/or 1695b) or receiving signal 1696a (and/or 1696b). Whole bottle system 1601 can be connected to intranet through private network (e.g. home network), and/or intranet through wired/wireless network. In the block diagram input signal is generated through the sensor 1672. The sensor 1672 may be one of a variety previously listed, such as, but not limited to a pressure sensor, lights, accelerometer, proximity, pulse oximeter blood pressure sensor, glucose meter, or combination thereof. The sensor 1672 can receive power from the power circuitry (not shown here) whose source could be directly from power supplies, battery, capacitor (used for energy storages), energy storage, or combination thereof. In amplification unit 1677, the signal from a sensor is amplified from the level captured by the sensor 1672. Amplification can be done through a variety of means, including but not limited to, low noise (LNAs), variable gain amplifiers (VGAs), and/or other amplification systems and circuitry. Noise cancellation may take place within the amplification or before or after through the use of other subsystems and circuitry. The main differences in FIG. 16C, as compared with FIGS. 16A and 16B, are that the analog signal after amplification and noise cancellation unit 1677 which has multiple signal paths: one to (the infrared) diode 1608 and another path is to the Analog to Digital Conversion Unit 1682. The noise cancellation may be done through feedback loops, filters in analog domain in order to condition the signal and for sampling in the analog signal after amplification and/or noise cancellation pass through the ADC unit 1682. The diode 1608 generates the light signal 1609 and transmits to the photo detector, located close proximity to the diode 1608 to convert the light signal to electrical signal and sends to the RF signal processing unit 1618 to transmit to the communication device. The Diode unit 1608 and 1613 units can be paired with the light diode and detector for each case to transmit and receive the information from and the bottle system. The RF signal processing unit to receive for receiver can also work in reverse way. For example, In reverse case, especially receiving case, RF receiver (not shown here) signal after received by the RF receiver (pair with the Transmitter) then send to the nearest IR diode (not shown here) which could be paired with the photo detector 1613 as IR diode (not shown here) to transmit to the nearest photo detector (not shown here) and paired with IR diode 1608 to send the signal to the bottle system to extract the data and/or input the data (not shown here). In the alternative embodiment, different from FIG. 16C, the diode 1608 and the photo detector (also mentioned as detector) 1613 can be either as separate component, with or without paired with detector and diode (not shown here) for transmitter or receiver aspect. The diode 1608 and detector 1613 can be integrated with the RF signal processing unit to have both transmitter/receiver capability to send/receive signal from the bottle (not shown here). In alternative embodiment, the diode 1608 and detector 1613 can be integrated with the bottle and/or caddy to have both transmitter/receiver capabilities to send/receive signal from the bottle (not shown here). In alternative embodiment, not shown in FIG. 16C, prior to sending the signal to diode 1608, the signal can be converted to digital (not shown here) and launch to the photo detector (receiver) 1613 which can be linked to RF signal processing unit 1618 with an additional capability of digital to analog conversion (not shown here). In this processing unit 1618, the signal is conditioned and sampled so that it can be modulated and wirelessly transmitted. Additionally, 1618 may be able to receive signal can transmissions and communicate back to the bottle through the use of 1613 and 1608 with their paired detector/ detector system.

The ADC unit 1682 using in FIGS. 16A to 16B will have a wide range of specifications, which include, but not limited to resolution, dynamic range, and sampling speed. These speculations are largely dependent on the type of sensor and requirement for the bottle system.

The ADC 1682 can have more than one connection, for example on can be connected to amplification unit 1677, others are to signal processing unit 1687 and the control unit 1692. Additional circuitry may require in between each unit for achieving better and/or additional performances (not shown here). In the processing unit 1687 the signal is conditioned, corrected, and/or compared with reference/ prior information to estimate/update to the current information. The processing unit 1687 comprise of a digital signal processor, a central processing unit microcontroller unit or any combination thereof. In the processing unit 1687, the signal is analyzed, updates memory and sends the information processed to the display 1620 and to the control unit 1692. The control unit 1692 is connected to the ADC 1682 and controls how the incoming signal from the amplification unit 1677 is digitally filtered and the sample rate is selected. The processing unit 1687 is also electrically connected to the display 1620 and sends the appropriate signals depending on the display type, LCD, LED for example. The signal processing and store unit is also connected to a Bluetooth transmitter and receiver 1623. Here the digital signal is encoded and modulated to the Bluetooth band and sent to any connected device (e.g. personnel computer, phone). Connected devices are represented as a communication device 1628 which is connected to distant communication device through internet 1697 and/or public network, or other proprietary network. The connected devices represent a wide variety of devices, such as but not limited to personal computers, mobile devices or other proprietary means. The connected devices may receive a notification or be able to manage the regulation of the bottle as mentioned in the detail from FIGS. 14A to 15B.

The user interface (not shown here), mentioned in FIGS. 15A and 15B is connected to the signal processing unit which receives signal after converting analog signal from the sensor to digital data and data processing is done using the processor or DSP or FPGA. The processing unit as shown in FIGS. 16A to 16C may receive data/signal from the user interface (not shown here), the sensors, or a combination thereof. In the case that the processor unit is integrated into the sensors then the output of the processor can be sent to the user interface over the internal communication path (not shown here). The processing unit can process the sensor data, perform analysis, and update the user interface to feedback, advice or signal the user. The processing unit in FIGS. 16A, 16B, and 16C is contemplated to keep a log of its operation in a local database (not shown here) having non-transitory computer readable medium or in a remote database in communication means having non-transitory computer readable medium, and to which the Bottle or carrier may connect via radio such as WiFi or cellular network. As an illustrative example, the user interface can be an interactive means and/or communication means (e.g. PC, mobile, smartphone) that connects to a home network through home WiFi network, to the clinic or Hospital network via public network or to the Internet via cellular radio transmission receiving network, or combination thereof. As noted earlier, but not shown here however, pill bottle and/or carrier can further include other sensor which can provide the user/patient or their distant person with feedback of the user/patient's wellness through detecting user/patient's blood-pressure, heart-rate, oxygen concentration, glucose level, facial image etc. or combination thereof, and by showing the information to the display in another mode of operation.

Figure 17A:
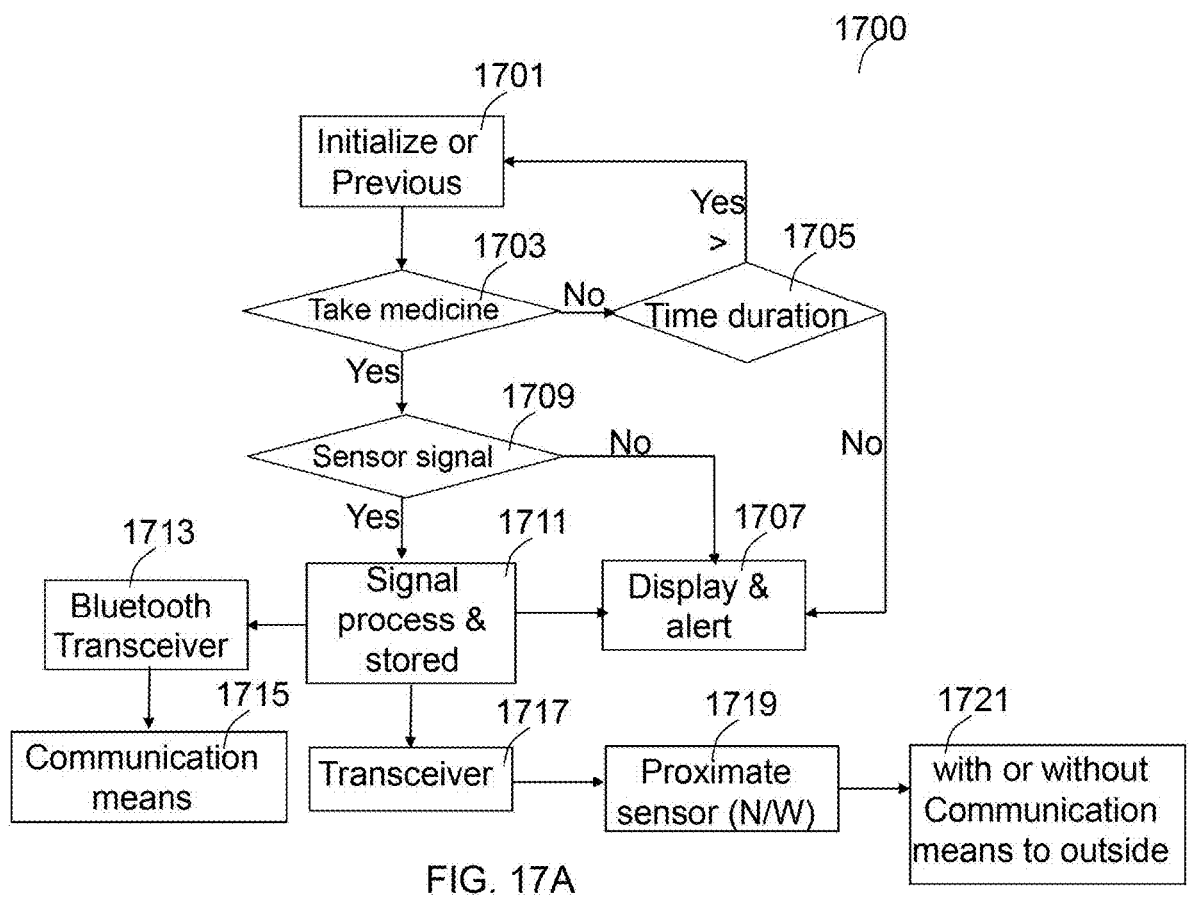
FIG. 17A is an example of the steady state operation of the pill bottle, with the steps need in order to successfully track the dosages taken in the preferred embodiment
Figure 17B:
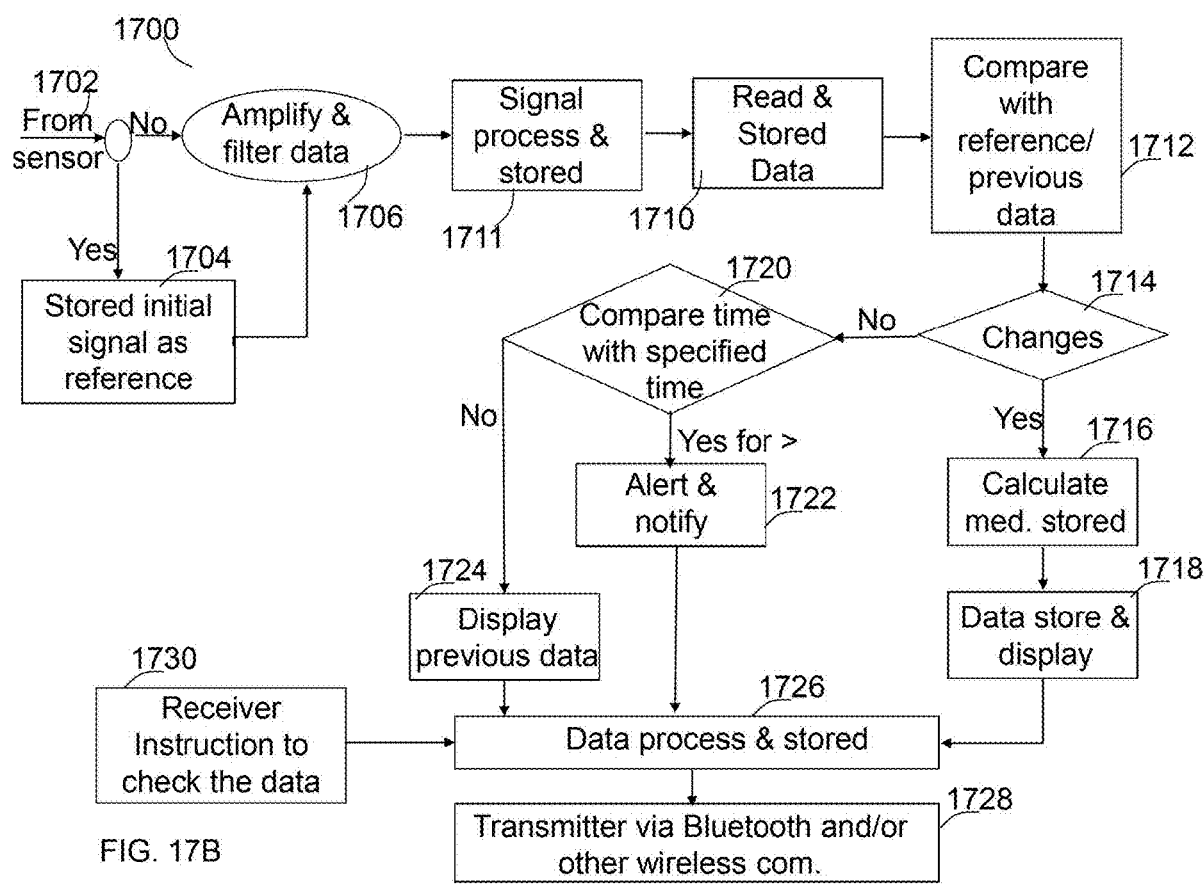
FIG. 17B is an example of alternate embodiment for the operation of the pill bottle for processing the data in the bottle system and its interaction with communication means in the preferred embodiment.

FIGS. 17A and 17B illustrate flow chart, showing exemplary of operation and associates functionality of a bottle system. In order to provide additional context for various aspects thereof, FIGS. 17A and 17B and the following discussion are intended to provide a brief, general description of a suitable environment in which the various aspects of the innovation can be implemented. While the description includes a general context of electronic means (e.g. computer) based executable instructions, those skilled in the art will recognize that the innovation also can be implemented in combination with other modules and/or as a combination of hardware and software. In order to provide additional context for various aspects thereof, FIGS. 17A to 17CB and the following discussion are intended to provide a brief, general description of a suitable environment in which the various aspects of the innovation can be implemented. While the description includes a general context of electronic means based-executable instructions which can be located in the bottle or/and in the communication device, those skilled in the art will recognize that the innovation also can be implemented in combination with other program modules and/or as a combination of hardware and software. FIG. 17A is the flow chart, illustrating a method of obtaining and providing updates from bottle to communication devices in the preferred embodiment according to the invention. The bottle system (not shown here) is initialized in 1701 and this function is done in pharmacy or doctor office that supplies the medications and/or provide the bottle. Alternatively, this function can be initiated at the patient/user location either by the patient/user or caretaker or caregiver, or combination thereof. Initialization is the time or starting time or refilling time or the time from when the medication is to be taken. At 1701, initialization is done and it will show the quantities of medication filled/refilled in the bottle. It also provides the information how much medication (e.g. pills) are left after each intake. This at 1701 stage also indicates the steady state operation is noted as initialize or previous. In this state, nothing will happen to the device unless there is an input, either external or internal providing a signal/information to the processing components to change the state of the system. Once a data is input, or the medication has been taken, the bottle system moves to the next state to 1703, if there has been medicine taken. Hence, the bottle measures/calculate the quantity from an previous/reference value, for example weight, and measures the difference between previous quantity and the new current value. If no difference is found in the measurement, then the state moves to 1705 where it counts the time duration of the event especially the time difference between the previous event to the current time where the event is supposed to be occurred or If the time difference is low or non-existent, then the bottle returns to the previous state which is 1701 In the occasions, wherein the difference is significant, the time is sent to be displayed in the display 1707 as an alert. The similar function can be also done simultaneously or separately by comparing the sensor value (quantities of pills for example) in 1709 and the expected value and the bottle sends similar data to the display with alert. If the event of taking medication is happened by opening of the bottle for example, sensor signal at 1709 sends the data to the processing unit 1711 where the signal is processed and stored the data and also sends to the display the resulting information data in the display in 1707. In another embodiment, the processing unit also sends the data to peripheral unit 1713 (e.g. Bluetooth transceiver) to transmit and/or receive the data to/from the nearest communication means device 1715 using wire or wireless using home/private network. The processing unit 1711 can also send the signal to other transmitter/receiver unit 1717 either connected by wire or wireless. At 1717, the signal can send to the proximate sensor 1719, located close to the bottle (not shown here) via private or home network and also further sends the processing data to the communication means or device 1721 to the outside world via internet or radio/wireless network. Alternatively, the data from processing unit to communication device can be sent/receive by/from any wireless network and the same device can also be sent to the distant communication means via wireless network. FIG. 17B is a flow chart, illustrating an alternative method of obtaining and providing updates from bottle to communication devices in the preferred embodiment according to the invention, wherein similar numeral represents a like part as shown in FIG. 17A, therefore, repeated explanation is omitted here. The main difference bottle system 1700 in FIG. 17B as that of FIG. 17A are that the sensor signal 1702 sends to the amplify unit 1706 if the signal is obtained not as initial (e.g. reference) signal 1704 wherein reference signal represents a signal obtained before using the bottle and the initial signal is stored as the reference signal which represents that bottle has been filled/refilled and not yet used/opened for medication. After amplification in amplify unit (and/or filter for noise cancellation) 1706, the signal is sent to the processing unit 1711 where data is processed and/or compared with the reference signal (not shown here) to provide information of medication intake, date, duration, behavior, others information based on the type of sensor being used in the bottle system, or combination of thereof. The information/data from 1711 is read and stored in 1710, and also compared with prior/reference data in 1712 to check if the changes 1714 are occurred in the bottle, or patient condition (known from the sensor system). If the changes are found in 1714, accurate count of med is calculated in 1716 and the data is stored and display in 1718. In the case of no changes is found in 1714, the time interval (duration) is calculated, wherein the time interval is the time duration between the time elapsed from medication taken previously and the time where the medication is to be taken, and the time of medication is to be taken is dependent on the specified time which was prescribed at the doctor office to take the medication. If the time-duration is found in 1720 to be more than the specified time (for example each 8 hr, to take the pill, and here 8 hrs is the time-duration), then the alert is to be given in 1722 to notify the patient/user or conveyed to the distant relatives, caretaker, caregiver, or the person to whom the notification is to be sent. If the time duration as shown in 1720 is less than the specified time (suggested in doctor office), then the stored data to be shown in display 1724 (or 1718) is the prior data. The notification information from 1722, 1718, and/or also from 1724 can be sent as an example either with processing the information in 1726 or without processing the information to the transmitter 1728 to communication device. The transmitter can be comprised of peripherals functional module which comprises of Bluetooth, wired, wireless, or others means via which data can be transmitted to the communication device in both the communication devices, located in close proximity and/or located in the distant place (not shown here). The bottle system can be also interactive with patient/user, pharmacy administrator, doctor office, caretaker, caregiver by sending the information to bottle system via receiver 1730 to get the data stored to know the statistics (an example) over the specific period of time/date/months/year. The receiver system 1730 can be integrated with transmitter system 1728, and/or completely independent receiver system. The module provided and also their related functional explanation for both FIGS. 17A and 17B are related to transmitter functionality. In reverse way, the bottle system can be come with the receiver system to provide the interactive functionality from the communication device, either located close proximity or in the distant location. The receiver system can be integrated with the transmitter which can be treated as transceiver, or completely independent with each other. The bottle system can process IP data traffic via the communications device to accommodate IP traffic from an IP network such as, for example, the Internet, a corporate intranet, a home broadband network, a personal area network, etc., via an ISP or broadband cable provider. Thus, VoIP traffic can be utilized by the bottle system and IP-based multimedia content can be received in an encoded and/or decoded format.

The displays 1707 in FIG. 17A and 1724 (and/or 1718) in FIG. 17B for displaying multimedia that include text, images, video, telephony functions (e.g., a Caller ID function), setup functions, menus, etc. The displays as shown in FIG. 17A and FIG. 17B can also accommodate the presentation of multimedia content (e.g., music metadata, messages, wallpaper, graphics, etc.).

An input/output (I/O) interface (not shown here) optionally can be provided for serial/parallel I/O of data and/or signals (e.g., USB, and/or IEEE 1394) via a hardwire connection, and other I/O devices (e.g., a keyboard, keypad, mouse, interface tether, stylus pen, touch screen, etc.). The I/O interface can be utilized for updating and/or troubleshooting the bottle system, for example.

In alternative embodiment, audio capabilities can also be provided via an audio I/O component (not shown here), which can include a speaker for the output of audio signals related to, for example, indication that the user pressed the proper key or key combination to initiate the user feedback signal, call signals, music, etc. The audio I/O component also facilitates the input of audio signals via a microphone to record data and/or telephony voice data, and for inputting voice signals for telephone conversations. Further, it may provide warning to the patient/user and/or provide alert to the caregiver/physician/pharmacy personnel, if the overdoses is detected in the system.

In an alternative embodiment the computer or programmable device that stores the prescription schedule or the bottle is located at a pharmacy, physician's office or hospital. The bottle will be in communication with the computer system through wireless networks, the internet, or other means. The computer or programmable device which is programmed with the prescription schedule may only be modified by the pharmacy, physician's office or hospital that the computer or programmable device is stored. Computer will send information to the bottle to remind the user of when to take a dose, how much to take and other information as shown in the above embodiments. The bottle will send information back to the computer from its sensors. The information from the sensor may include data regarding when doses are taken, the amount taken, whether medication is missing, or of the patient is not taking the medication at regular intervals or at all. This information allows the computer to determine the doses taken by the patient and whether corrective action is required. Circumstances where corrective action is required involves situations where the patient is taking more or less medication than the prescription schedule prescribes.

Depending of the nature of the medication the failure to take the medication on time may have significant adverse affects. Furthermore of the medication is a controlled substance such as an opiate then the sensor sensing that the medication has been taken too fast, or a sudden does on the supply of doses in the bottle may indicate that the need for corrective action. Because the smart bottle with the sensor is able to report back to the pharmacy, physician's office or hospital, when medication is taken or missing, the smart bottle acts as a deterrents to abusing harmful medications. Alternatively, if the smart bottle senses too many of the doses taken in a short period of time it may indicate that the life of the patient is at risk and alert emergency services.

The computer system stored at the pharmacy, physician office, or hospital may only be programmable by the pharmacy, physician office, or hospital in order to prevent tampering by the patient.

The smart bottle system may have a locking mechanism, which prohibits the patient from taking the medication at the wrong times. Such a mechanism will be, used on medications that may be dangerous when taken too often. The locking mechanism may be used along side a dispensing system that controlled the amount of medication dispensed at each dose. Such systems may be used to prevent suicides, or overdoses. This system also acts as a deterrent to crimes, as the smart bottle reports back to another computer and records information, that may be used to catch someone stealing the bottle, or its contents.

The locking mechanism includes, but not limited to biometric of authorized user which may include, but not limited to, patient, caregiver, nurse, physician, pharmacy personnel, family members, or combination thereof.

Alternatively, the smart bottle system may be part of a Telemedicine or e-medicine system. The smart bottle is programmed by the doctor, and provides feedback, to the doctor's office, in order to keep the doctor informed to the patient's condition. The Smart bottle would be one part in a larger system that provides information to the doctor on the patient's condition and allows for doctor to make decisions on the patient's treatment.

An exemplary embodiment of the smart bottle system is a smart bottle that is in communication with the computer system located in the pharmacy that filled the prescription. The pharmacy programs the prescription into the computer system, and the computer system transmits the time to take the medication to the smart bottle, which displays the time to take the medication, and alerts the patient. The smart bottle then provides feedback to the computer system when the patient has taken the medication and from sensor s on the bottle the amount, or an approximation of the amount of medication left in the bottle. If the information from the sensors indicate that to much medication is taken, depending on the specific medication, patient, and circumstances, the computer system may alert the patient, a caregiver, the physician or emergency services to a lethal dose of medication being take, or a amount of controlled medication has gone missing.

A further iteration of the of the above embodiment the smart bottle may be equipped with a locking mechanism, and/or a dispensing mechanism in order to prevent the patient from taking to large a dose at one time.

In another embodiment, the bottle can have an emergency button (not shown here) which is located visible side of the bottle. When the button is pressed, it immediately alerts the nearest emergency personnel to come to the patient's location. To prevent any false alarm, a phone call or text message will be sent to confirm the emergency. If the patient doesn't respond in a window of specific time (i.e. fifteen minutes), then an emergency personnel will be sent to the patient's current location without any confirmation. Pressing the emergency button will also alert family member (i.e. loved one), a caregiver, by sending them an automated text or voice message.

In another embodiment, the bottle can have a thermal barrier/patch around its side and this will prevent the medicine from heating or cooling depending on its environment. The thermal insulator helps to keep the medicine at an optimal temperature (59-86 Fahrenheit) to prevent the medication from decaying or getting damaged. Further, a temperature sensor (not shown here) in the bottle will warn the patient during times of extreme heating or cooling of the surrounding environment. The warning will come in two forms. The first form of warning can appear on a communication device (i.e. smart phone). The second form of warning may appear on the bottle as a flashing a light (i.e. red) for extreme temperature and another color (i.e. green light) for optimal temperature. To prevent the medication from decaying or getting damaged, the sensor will send a message to the patient's phone, for example.

In another embodiment, the bottle can have also a lock on it and it can be controlled by a click of a button through the application on the smart phone. The lock prevents children from accidentally opening the container and consuming the medication. There is also an automatic lock whenever the patient's medication expires. This prevents the patient from swallowing a medication that lacks potency without his or her consideration. An additional biometric lock system can also be used for patients that do not own a smart phone. A biometric lock on the cap provides security and safety of the medication. In another embodiment, the camera system or similar means thereof, located on the bottle and/or outside the bottle, close proximity to the bottle can provide the information of the patient facial condition and others (not mentioned here) which is necessary to project the health condition of the patient using the computing device or similar means either embedded and/or outside device.

The alarm system (1193 in FIG. 11C, as an example) of the bottle will have different modes. For sick patients, a calm and soothing sound will be played to remind them to take their medication. The settings of the different sounds can be controlled through the smart phone device via Bluetooth. The sounds can include music or a pre-recorded message or procedure from a family member, caregiver, or a doctor. The sound can be administered by the patient, family member, caregiver, or a doctor.

The smart phone application will contain all the specific information of the drug that the patient is taking. The information includes: dosage, name of the drug, Drug Company, and an image of the drug. This will help patients to obtain their needed medication during times when they are out of town.

Whereas many alterations and modifications of the present invention will no doubt become apparent to a person of ordinary skill in the art after having read the foregoing description, it is to be understood that the particular embodiments shown and described by way of illustration are in no way intended to be considered limiting. Therefore, reference to the details of the preferred embodiments is not intended to limit their scope.

The embodiments are chosen and described in order to explain the principles and applications of the invention, thereby allowing others skilled in the art to utilize the invention in its various embodiments and modifications according to the particular purpose contemplated. The scope of the invention is intended to be defined by the claims appended hereto and their equivalent.

As used in this application, the terms "component" and "system" are intended to refer to a computer-related entity, either hardware, a combination of hardware and software, software, or software in execution. For example, a component can be, but is not limited to being, a process running on a processor, a processor, a hard disk drive, multiple storage drives (of optical and/or magnetic storage medium), an object, an executable, a thread of execution, a program, and/or a computer. By way of illustration, both an application running on a server and the server can be a component. One or more components can reside within a process and/or thread of execution, and a component can be localized on one computer and/or distributed between two or more computers.

The following discussion is intended to provide a brief, general description of suitable processor-based devices or systems in which the various aspects can be implemented. Those skilled in the art will recognize that a novel embodiment also can be implemented in combination with other program modules and/or as a combination of hardware and software.

Generally, program modules include routines, programs, components, data structures, etc., that perform particular tasks or implement particular abstract data types. Moreover, those skilled in the art will appreciate that the inventive methods can be practiced with other processor-based configurations, including single-processor or multiprocessor systems, as well as personal computers, hand-held or embedded computing devices, microprocessor-based or programmable consumer electronics, and the like, each of which can be operatively coupled to one or more associated devices.

A processor-based system typically includes a variety of computer-readable media. Computer-readable media can be any available media that can be accessed and includes volatile and non-volatile media, removable and non-removable media. By way of example, and not limitation, computer-readable media can comprise computer storage media and communication media. Computer storage media includes volatile and non-volatile, removable and non-removable media implemented in any method or technology for storage of information such as computer-readable instructions, data structures, program modules or other data. Storage media includes, but is not limited to, RAM, ROM, EEPROM, flash memory or other memory technology, CD-ROM, digital video disk (DVD) or other optical disk storage, magnetic cassettes, magnetic tape, magnetic disk storage or other magnetic storage devices, or any other medium which can be used to store the desired information and which can be accessed by the communication device or computer.

The system is operable to communicate with any wireless devices or entities operatively disposed in wireless communication, for example, a printer, scanner, desktop and/or portable computer, portable data assistant, communications satellite, other hubs, mobile phones, any piece of equipment or location associated with a wirelessly detectable tag (e.g., a kiosk, news stand, restroom), and telephone. This includes at least Wi-Fi, WiMax, and Bluetooth™ wireless technologies, for example. Thus, the communication can be a predefined structure as with a conventional network or simply an ad hoc communication between at least two devices.

What has been described above includes examples of the disclosed architecture. It is, of course, not possible to describe every conceivable combination of components and/or methodologies, but one of ordinary skill in the art may recognize that many further combinations and permutations are possible. Accordingly, the novel architecture is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A smart bottle system comprising:
   a bottle, wherein the bottle comprises;
      an inside surface, and;
      an outside surface;
   a lid, wherein the lid is interchangeable from one bottle to another;
   a display, wherein the display is located on the outside surface of the bottle body;
   an, energy storage device;
   a sensor;
      wherein the sensor detects when the lid is opened and counts a medication taken;
   a programmable device;
   a computing device;
   a camera, and;
   a transponder, wherein the transponder comprises;
      a transmitting and/or;
      a receiving means;
   wherein the programmable device is programmed with a prescription information, wherein the computing device counts the medication usages and/or medication left from a counts information from the sensor, and sends an information to the display, wherein the transponder sends or receives the information to or from a person or a user via a communication media, and wherein the camera gets an image information of the user, wherein the computing device estimates the health condition and a profile and transmits to the person via communication media.

2. The smart bottle system of claim 1, further comprises a carrier/caddy, wherein the carrier/caddy provides power to the bottle, wherein the bottle and the carrier/caddy are in contacts or proximately located from each other.

3. The carrier/caddy according to claim 2 relays the information to a pharmacy/physician regarding the user's dose taking habits and/or when a next refill is required.

4. The smart bottle system of claim 1, wherein the display, further displays to take a next medication time.

5. The smart bottle system of claim 1, further comprises a alert mean or the display alerts to the user to take the medication, wherein the alert mean is a light that lights up or blinks, when the medication is to be taken.

6. The smart bottle system of claim 1, further comprises a button, wherein the button is located on the outside surface of the bottle.

7. The communication media according to the smart bottle system of claim 1, comprises a single or multiple mean and communicates through wireless communication.

8. The sensor according to the smart bottle system of claim 1, comprises a light emitter, and a light receiver/detector, wherein the light emitter emits light and the light receiver detects light, and wherein the sensor is located on the inner surface of the lid.

9. The smart bottle system of claim 1, wherein the display, further displays a digital clock that counts down to or shows the next medication time.

10. The communication media according to claim 1 relays the health information and/or the user's dose taking habits, and/or when a next refill is required to a pharmacy/physician or to a care taker.

* * * * *